United States Patent
Streiff

(10) Patent No.: US 11,622,724 B2
(45) Date of Patent: Apr. 11, 2023

(54) SURFACE ANALYSIS PATCH

(71) Applicant: SYNEWORK.COM, Zurich (CH)

(72) Inventor: Matthias Streiff, Zurich (CH)

(73) Assignee: SYNEWORK COM, Zurich (CH)

(*) Notice: Subject to any disclaimer, the term of this patent is extended or adjusted under 35 U.S.C. 154(b) by 634 days.

(21) Appl. No.: 16/349,298

(22) PCT Filed: Nov. 14, 2017

(86) PCT No.: PCT/EP2017/079142
§ 371 (c)(1),
(2) Date: May 13, 2019

(87) PCT Pub. No.: WO2018/091439
PCT Pub. Date: May 24, 2018

(65) Prior Publication Data
US 2020/0178894 A1 Jun. 11, 2020

(30) Foreign Application Priority Data
Nov. 15, 2016 (EP) .................................... 16198917

(51) Int. Cl.
A61B 5/145 (2006.01)
A61B 5/00 (2006.01)

(52) U.S. Cl.
CPC ........ *A61B 5/6833* (2013.01); *A61B 5/14546* (2013.01); *A61B 2562/0223* (2013.01)

(58) Field of Classification Search
USPC ....................................................... 600/309
See application file for complete search history.

(56) References Cited

U.S. PATENT DOCUMENTS 4,450,844 A 5/1984 Quisno
5,441,048 A * 8/1995 Schoendorfer ...... A61B 5/4266
600/346
(Continued)

FOREIGN PATENT DOCUMENTS

EP 1262559 12/2002
WO 99/13336 3/1999

OTHER PUBLICATIONS

R. Lazzarini et al: "Patch tests", Anais Brasileiros De Dermatologia (Sociedade Brasileira De Dematogogia), vol. 88, No. 6, Dec. 1, 2013, pp. 879-888.

*Primary Examiner* — Alex M Valvis
*Assistant Examiner* — Aurelie H Tu
(74) *Attorney, Agent, or Firm* — JMB Davis Ben-David

(57) ABSTRACT

A flexible planar patch suitable for application to a patient's skin is provided. The planar patch comprises a capture layer (100) and a cover layer (200). The capture layer (100) comprises an analyte capture zone (105) and a fastener zone (104). The analyte capture zone (105) consists of a first water permeable material comprising a ligand capable of binding specifically to an analyte. The fastener zone (104) is impermeable to water and/or delimited from said analyte capture zone by a water impermeable barrier zone (108) and comprises an adhesive (133) capable of fastening the capture layer (100) removably to a surface. The cover layer comprises an adhesive (233) capable of fastening the cover layer (200) removably to the capture layer (100). In addition, a kit for assembly of the patch and a diagnostic method using the patch are provided.

20 Claims, 7 Drawing Sheets

(56) References Cited

U.S. PATENT DOCUMENTS

| | | | | |
|---|---|---|---|---|
| 5,445,147 A | * | 8/1995 | Schoendorfer | A61B 5/415 600/362 |
| 2006/0051738 A1 | * | 3/2006 | Zweig | G01N 33/523 435/4 |
| 2008/0300508 A1 | * | 12/2008 | Tomer | A61B 5/150412 600/583 |
| 2009/0076340 A1 | * | 3/2009 | Libbus | A61B 5/721 600/301 |
| 2013/0267809 A1 | * | 10/2013 | Brister | A61B 5/14503 600/347 |
| 2014/0357964 A1 | * | 12/2014 | Wisniewski | A61B 5/742 600/301 |
| 2015/0335288 A1 | * | 11/2015 | Toth | A61B 5/6833 600/373 |

* cited by examiner

SURFACE ANALYSIS PATCH

CROSS-REFERENCE TO RELATED APPLICATIONS

This is the U.S. National Stage of International Patent Application No. PCT/EP2017/079142 filed on Nov. 14, 2017, which was published in English under PCT Article 21(2), which in turn claims priority to European Patent Application No. 16198917.3 filed on Nov. 15, 2016.

The present invention relates to a dermal patch for multiplexed point of care diagnosis of skin conditions.

BACKGROUND

Point of care testing (POCT) refers to medical diagnostic testing at or near the time and place of patient care. The essential advantage of POCT is that it does not require samples to be sent to a laboratory for analysis. Instead, results are obtained and interpreted immediately. This kind of diagnosis is especially relevant for physicians that are not associated with bigger hospitals or institutions.

POCT testing uses rapid diagnostic tests that are quick and easy to perform. A common example are lateral flow tests.

For the diagnosis of skin conditions, dermal diagnostic patches have been developed. U.S. Pat. No. 4,450,844 describes a patch system for applying samples or drugs to a person's skin. The patch system comprises a flexible housing containing the compound to be applied and a cover sheet made of adhesive tape. Lazarrini et al. (An Bras Dermatol. 2013; 88(6):879-88) provides an overview of patch tests for the diagnostic investigation of contact dermatitis. These patches plant a substance known to be causative for certain forms of contact dermatitis on the patient's skin. After 1-2 days, the patch is removed and it is determined which substance has caused a local allergic reaction. WO99/13336 describes a transdermal patch for collecting and detecting an analyte (e.g. glucose) in a biological fluid in or underneath the skin. The patch comprises a wet component and a dry component. The dry component is a membrane comprising reagents specifically reacting with the analyte of interest. The wet component comprises a liquid reservoir comprising a transfer medium for the collection of analytes. EP1262559 describes a dermal patch for detecting lactate. The patch comprises one or more reagent layers containing regents for specifically detecting lactate.

Patches known in the art however are often not suitable for POCT as they take too long to deliver results or are not realizable in the setting of a small dermatologist or family doctor practice. Patches that are suitable for POCT do not allow easy multiplexing of more than 5 analytes or do not allow conducting parallel replicates for analytes present at low concentrations. Replicates are however an important prerequisite to improve accuracy in order to obtain quantitative results. In addition, existing patches do not allow for parallel detection of analytes with incompatible detection protocols (protocols requiring reagents that are incompatible).

The problem underlying the present invention is to provide the means and methods for fast and easy detection and quantification of multiple analytes involved in skin conditions. This problem is solved by the subject-matter of the independent claims.

DETAILED DESCRIPTION OF THE INVENTION

According to a first aspect, a flexible planar patch is provided. The patch is suitable for application to a patient's skin or mucous membrane. The planar patch comprises a capture layer (100) and a cover layer (200).

a. The capture layer (100) has a proximal surface (101) and a distal surface (102). In instances where the planar patch is applied to a surface for analyte collection, the proximal surface (101) of the capture layer (101) faces towards this surface and the distal surface (102) of the capture layer (100) faces away from it.

The capture layer (100) is characterized by a thickness of 10 µm to 2 mm. In certain embodiments, the capture layer (100) is characterized by a thickness of to 25 µm to 1 mm. In certain embodiments, the capture layer (100) is characterized by a thickness of 50 µm to 500 µm. In certain embodiments, the capture layer (100) is characterized by a thickness of approximately 200 µm.

The capture layer (100) comprises an analyte capture zone (105) and a fastener zone (104).
  i. The analyte capture zone (105) extends from the proximal surface (101) to the distal surface (102). The analyte capture zone (105) consists of a first water permeable material. In certain embodiments, the first water permeable material is capable of transporting an aqueous solution. In certain embodiments, the first water permeable material is capable of transporting an aqueous solution by capillary force. In certain embodiments, the first water permeable material is nitrocellulose or polyester non-woven backed nitrocellulose. The first water permeable material comprises a ligand capable of binding specifically to an analyte. In particular, the ligand is located at the proximal and/or distal surface of the analyte capture zone (105). Binding between ligand and analyte primarily takes place close to the proximal or distal surface of the analyte capture zone (105).
  ii. The fastener zone (104) is impermeable to water and/or delimited from said analyte capture zone by a water impermeable barrier zone (108). In certain embodiments, the water impermeable barrier zone (108) is composed of a hydrophobic material selected from the group comprising a wax, a thermoplastic polymer, a thermoplastic copolymer, in particular thermoplastic polyurethane, an epoxy, and an adhesive. The fastener zone (104) comprises, on the proximal surface (101), an adhesive (133) capable of fastening the capture layer (100) removably to a surface.

b. The cover layer (200) has a proximal surface (201) and a distal surface (202).

The cover layer (200) is characterized by a thickness of 10 µm to 3 mm. In certain embodiments, the cover layer (200) is characterized by a thickness of to 25 µm to 1 mm. In certain embodiments, the cover layer (200) is characterized by a thickness of 50 µm to 500 µm. In certain embodiments, the cover layer (200) is characterized by a thickness of approximately 400 µm.

The cover layer comprises, on the proximal surface (201), an adhesive (233) capable of fastening the cover layer (200) removably to the distal surface (102) of the capture layer (100).

In the context of the present specification, the "water impermeable barrier zones composed of hydrophobic material" and the "dividers composed of a zone of hydrophobic material" are made by introducing a hydrophobic material into a water permeable material. The water permeable material may be the first water permeable material of the analyte capture zone (105) (described above) or the second water permeable material of the reagent zone (205) (described below). The hydrophobic material is selected from wax, epoxy, solid ink, hotmelt, hotmelt ink, polyester or other thermoplastic material as well as dry or liquid photoresist, or UV curable ink, and is introduced into the water permeable material by inkjet printing, screen printing, tampon printing, offset printing, or laminated to the membrane, cured by heat, light, activator, or a combination thereof.

The term "removably attached" in the context of this specification refers to an attachment between two objects, particularly cover layer (200) and capture layer (100) as well as capture layer (100) and rigid support (300), that is characterized by a peel adhesion of 0.1-5 N/25 mm. "Peel adhesion" is defined as the force required to remove a pressure sensitive tape from a surface at a controlled angle and at a standard rate and condition.

In certain embodiments, the dimensions of the patch are approximately 25 mm×25 mm.

The removable attachment between capture layer (100) and surface enables repeated attachment and removal of the patch to different surfaces. In a typical example, the patch is first attached to a surface for analyte collection. The flexible nature of the patch makes it suitable for application to curved surfaces like a patient's skin or mucous membrane. The possible applications of the patch are however not limited to these surfaces. The patch allows analysis of analytes obtained from other surfaces such as walls, floors, door handles and door knobs, as well as processing of other samples such as cell lysates, tissue extracts, serum, plasma, derivatives of blood, full blood, saliva, or urine. After a suitable incubation time, the patch is removed and can now be attached to a different surface for the analysis steps. In certain embodiments, this surface is the rigid support (300) described in detail below.

The removable attachment between cover layer (200) and capture layer (100) enables repeated removal and re-attachment of a cover layer to the capture layer, in particular the removal of one cover layer and subsequent attachment of a different cover layer. In a typical example, a first cover layer (sampling cover layer, 200 P1) is used during sampling/analyte collection. Subsequently, during sample analysis, the first cover layer is removed and a second cover layer (analysis cover layer, 200 P2) is attached to the distal surface (102) of the capture layer (100). Optionally, the analysis cover layer (200 P2) is removed and replaced by a new analysis cover layer (200 P3, P4 . . . Pn). It is possible to subsequently attach and remove up to 7 cover layers without compromising the stability and functionality of the patch.

The term "ligand specifically binding to an analyte" in the context of the present specification refers to a molecule selected from antibodies, antigen binding fragments, aptamers, enzymes, pore and motor proteins for nucleic acid sequencing, receptors, proteins, nucleic acids, molecularly imprinted polymers, and crown ethers.

In the context of the present specification, the term "antibody" is used in its meaning known in the art of cell biology and immunology; it refers to whole antibodies, any antigen binding fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region ($V_H$) and a heavy chain constant region ($C_H$). The heavy chain constant region is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxyterminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

In the context of the present specification, the term "antigen binding fragment" is used in its meaning known in the art of cell biology and immunology; it refers to one or more fragments of an intact antibody that retain the ability to specifically bind to a given antigen (e.g., interleukin-2). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH domains; a F(ab)2 fragment, a bivalent fragment comprising two Fab fragments linked by a disulfide bridge at the hinge region; an Fd fragment consisting of the VH and CH domains; an Fv fragment consisting of the VL and VH domains of a single arm of an antibody; a single domain antibody (dAb) fragment, which consists of a VH domain or a VL domain; and an isolated complementarity determining region (CDR).

The term "binding specifically" in the context of the present specification relates to binding between ligand and analyte with a dissociation constant ($K_D$)≤10 E−7.

In the context of the present specification, the term "dissociation constant ($K_D$)" is used in its meaning known in the art of chemistry and physics; it refers to an equilibrium constant that measures the propensity of a larger object to dissociate reversibly into smaller components, as when a complex falls apart into its component molecules. $K_D$ is expressed in molar units [M] and corresponds to the concentration of [Ab] at which the binding sites of [Ag] are half occupied. In other words the concentration of unbound [Ab] equals the concentration of the [AbAg] complex. The dissociation constant can be calculated according to the following formula:

$$K_D = \frac{[Ab] * [Ag]}{[AbAg]}$$

[Ab]: concentration of antibody; [Ag]: concentration of antigen; [AbAg]: concentration of antibody-antigen complex The analyte capture zone (105) may additionally comprise an adhesive that binds to a plurality of analytes with little specificity.

The ligands are immobilized on the analyte capture zone (105). In certain embodiments, this is achieved by dispensing, pipetting, contactless ink jet printing, or a combination thereof.

Analytes that can be detected using the flexible planar patch according to the invention are bacteria, fungi, eukaryotic microbes; blood cells and fragments thereof; hyphae, pollen and spores; viruses, exosomes, proteins (including cytokines and chemokines), free DNA or RNA, and fragments thereof; smaller molecules, and ions. Other analytes that can be detected using the flexible planar patch according to the invention are parasites, e.g. parasites affecting humans or domestic animals. One non-limiting example of such parasites are helminthes, e.g. Echinococcus multilocularis, a tapeworm that causes echinococcosis.

The flexible planar patch according to the invention may also be used to examine the efficacy of an antibacterial drug. In these instances, the analyte to be detected is an intracellular bacterial component. If such an intracellular component is detected, this is an indication for the degradation of the bacterial cell wall and thus for the efficacy of the antibacterial drug.

Another possible application of the flexible planar patch according to the invention is to detect an infection by bacteria that are resistant towards a certain antibacterial drug. In these instances, the analyte to be detected is a bacterial component responsible for a known resistance mechanism, e.g. an enzyme able to degrade an antibacterial drug.

The analyte capture zone (105) serves as a selective barrier that filters analytes according to their size. In certain embodiments, the first water permeable material of the analyte capture zone is characterized by a pore size 10 μm. In certain embodiments, the first water permeable material of the analyte capture zone is characterized by a pore size 1 μm. In certain embodiments, the first water permeable material of the analyte capture zone is characterized by a pore size of 0.1-1 μm. In certain embodiments, the first water permeable material of the analyte capture zone is characterized by a pore size of 0.1-0.5 μm. Analytes with a diameter larger than the pore size do not pass the analyte capture zone (105) and can thus only be bound by ligands present on the proximal surface (101) of the capture zone (105). By way of non-limiting example, such larger analytes may be bacteria, fungi, or fragments thereof, such as cell membrane fragments.

Analytes with a diameter smaller than the pore size can pass the analyte capture zone (105). They can thus be bound by ligands present on the proximal surface (101) or the distal surface (102) of the analyte capture zone (105). By way of non-limiting example, such smaller analytes may be proteins, oligonucleotides or ions.

In certain embodiments, the analyte capture zone (105) is compartmentalized into a plurality of confined water permeable capture divisions (106). Each capture division comprises the ligand capable of binding specifically to an analyte. In certain embodiments, the analyte capture zone (105) is compartmentalized into 1-1000 capture divisions (106). In certain embodiments, the analyte capture zone (105) is compartmentalized into 1-256 capture divisions (106). Each capture division is separated from any other capture division by a first divider (107) that is impermeable to water.

The high number of capture divisions enables conducting parallel replicates as well as multiplexing. For parallel replicates, a group of (at least two) capture divisions (106) comprising the same analyte (in the same concentration) and the same ligand (in the same concentration) is treated with the same order of reagents. Results obtained for each capture division (106) of this group of capture divisions are averaged, thus increasing the accuracy of the measurement.

For multiplexing, a first capture division (106) comprises a first ligand, while a second capture division (106) on the same capture layer (100) comprises a second ligand different from the first ligand. This enables detection of more than one analyte with a single patch. Another application is to perform antibody cross-reactivity tests in which the reaction of approximately 100 different antibodies (each on a different capture division) against an antigen can be tested at once.

In certain embodiments, the plurality of capture divisions (106) is divided into groups of capture divisions (111). In certain embodiments, the plurality of capture divisions (106) is divided into 1-50 groups of capture divisions (111). In certain embodiments, the plurality of capture divisions (106) is divided into 1-16 groups of capture divisions (111). Each group of capture divisions is separated from any other group of capture divisions by a second divider (109) that is impermeable to water.

In certain embodiments, the capture zone (105) is located in the centre of said capture layer (100) and said fastener zone (104) is located at the perimeter of said capture layer (100). The fastener zone (104) surrounds the capture zone (105), thus providing structural support to said capture layer. Structural support is particularly important while the capture layer (100) is being attached to or removed from a surface during analyte collection, or while a cover layer (200) is being attached to or removed from the capture layer (100).

In certain embodiments, the peel adhesion between cover layer (200) and capture layer (100) is between 0.1 N/25 mm and 5 N/25 mm. In certain embodiments, the peel adhesion between cover layer (200) and capture layer (100) is between 0.5 N/25 mm and 4.5 N/25 mm. In certain embodiments, the peel adhesion between cover layer (200) and capture layer (100) is between 1 N/25 mm and 4 N/25 mm.

In certain embodiments, the cover layer (200) comprises a reagent zone (205) and a fastener zone (204).
  a. The reagent zone (205) extends from the proximal surface (201) to the distal surface (202). The reagent zone (205) consists of a second water permeable material. In certain embodiments, the first water permeable material is capable of transporting an aqueous solution. In certain embodiments, the first water permeable material is capable of transporting an aqueous solution by capillary force.
  b. The fastener zone (204) is impermeable to water and/or delimited from said reagent zone (205) by a water impermeable barrier zone (208). In certain embodiments, the water impermeable barrier zone (208) is composed of a hydrophobic material selected from the group comprising a wax, a thermoplastic polymer, a thermoplastic copolymer, in particular thermoplastic polyurethane, an epoxy, and an adhesive.

In certain embodiments, the reagent zone (205) is located in the centre of said cover layer (200) and said fastener zone (204) is located at the perimeter of said cover layer (200). The fastener zone (204) surrounds the reagent zone (205), thus providing structural support to the cover layer.

In certain embodiments, the reagent zone (205) is compartmentalized into a plurality of confined water permeable reagent divisions (206). In certain embodiments, the reagent zone (205) is compartmentalized into 1-144 reagent divisions (206). In certain embodiments, the reagent zone (205) is compartmentalized into 1-64 reagent divisions (206). In certain embodiments, the reagent zone (205) is compartmentalized into 1-36 reagent divisions (206). In certain embodiments, the reagent zone (205) is compartmentalized into 1-16 reagent divisions (206). Each reagent division is separated from any other reagent division by a reagent divider (207) that is impermeable to water.

The high number of reagent divisions (206) enables conducting parallel replicates as well as multiplexing. For multiplexing, a first reagent division (206) may comprise a first reagent, while a second reagent division (206) on the same cover layer (200) comprises a second reagent different from the first reagent. This enables the use of reagents that are incompatible with each other. Alternatively, all reagent divisions (206) of one cover layer (200) comprise the same reagent, but a solution releasing the reagent is only applied to a first subgroup of reagent divisions (206) which are in fluid connection with a first subgroup of capture divisions (106). Subsequently, this cover layer is removed from the capture layer and another cover layer (comprising reagent divisions comprising a different reagent) is attached to the capture layer. Again, the solution releasing the reagent is only applied to a second subgroup of reagent divisions (206) which are in fluid connection with a second subgroup of capture divisions (106).

In certain embodiments, the fastener zone (204) of the cover layer (200) comprise a lateral tab (209). The lateral tab enables easy removal of the cover layer (200) from the capture layer (100).

In certain embodiments, the reagent zone (205) comprises an adaptor (501). In certain embodiments, the adaptor (501) is designed to connect the reagent zone (205) to a confined volume, particularly the volume of a pipette or syringe.

During analyte collection, the capture layer (100) is attached to a surface (comprising the analyte) and the cover layer (200) is attached to the capture layer (100). A syringe or pipette containing an aqueous solution can be attached to the reagent zone (206) of the cover layer (200) via the adapter (501). By pressing the plunger of the syringe or pipette, the aqueous solution can be transferred from the syringe or pipette via the reagent divisions (206) and the capture divisions (106) to the surface. By releasing the plunger of the syringe or pipette (after an incubation time), the aqueous solution can be transferred from the surface via the capture divisions (106) and reagent division (206) back to the syringe or pipette. Optionally, the step of transferring the aqueous solution first to the surface and then back to the pipette may be repeated. The analyte is moved with the aqueous solution and is immobilized on the capture divisions if the capture divisions comprise a ligand specifically binding to said analyte. The directed movement of the aqueous solution using a pipette or syringe ensures the efficient transport of analytes from the surface to the analyte capture zone and the ligand comprised therein. The directed movement of analytes allows to decrease the incubation time on the surface and increases the amount of analytes transferred to (and bound in) the analyte capture zone, leading to an improved sensitivity of analyte detection.

The skilled person is aware that instead of using an adapter and syringe, the aqueous solution may also be added as a drop to the distal side of the reagent divisions, from where it will be directed via capillary force through the reagent divisions to the surface. After incubation, the aqueous solution may be moved back via the capture divisions and reagent divisions by placing an absorbent material (e.g. cellulose) above the reagent zone, or by a vacuum applied to the reagent zone.

In certain embodiments, the adaptor (501) is designed to connect the reagent zone (205) to an ultrasonic transducer. The ultrasonic transducer is advantageous during the analyte collection step, as it facilitates extraction of analytes, e.g. from the skin.

In certain embodiments, the reagent divisions (206) comprise a reagent. The reagent may be in dried, lyophilized, gel or aqueous form. In certain embodiments, the reagent is selected from the group comprising an acid, a base, a salt, a sugar, a surfactant, a protein, a nucleic acid, an antimicrobial agent, in particular an antibacterial and/or an antifungal agent, a dye (organic, inorganic, and solid state), a fluorophore, lanthanides, upconverting phosphor nanoparticles, colloidal gold, cellulose nanobeads, latex, a reagent for total protein quantification, an affinity molecule, in particular an antibody (primary or secondary), an aptamer, an enzyme, a molecularly imprinted polymer, a ionophore, a pore or motor protein for nucleic acid sequencing, a nanoparticle and a microbead. The reagents may be present 'as is' (in other words discretely/on their own) or they may be immobilised on microbeads or nanoparticles.

The microbeads and nanoparticles may be of magnetic or non-magnetic, and dyed or non-dyed kind. In the context of the present specification, an "upconverting phosphor nanoparticle" relates to a nanocrystal comprising phosphor. During fluorescent imaging applications, two or more low-energy photons (longer infrared wavelength) are absorbed by the phosphor followed by the emission of a single higher-energy photon (shorter visible wavelength): "upconversion" (Soukka et al., 2008, Ann. N.Y. Acad. Sci., 1130, 188-200).

In certain embodiments, the reagent divisions (206) comprise a reagent selected from an acid, a base, a salt, a sugar, a surfactant, a protein, a fluorophore, an upconverting phosphor nanoparticle, colloidal gold, a reagent for total protein quantification and an antibody.

In certain embodiments, the reagent divisions (206) comprise a primary antibody and a fluorophore. In certain embodiments, the reagent divisions (206) comprise a primary antibody, a secondary antibody and a fluorophore. In certain embodiments, the reagent divisions (206) comprise a primary antibody and/or a secondary antibody, a fluorophore, an ionic buffer, particularly a phosphate buffer, a sugar, particularly trehalose and/or sucrose, a surfactant, particularly poly vinyl pyrrolidone (PVP), and a blocking reagent, particularly bovine serum albumin (BSA). The skilled person is aware that the fluorophore can be covalently linked to the primary or secondary antibody.

The reagents are immobilized in the reagent zone (105), in particular between the proximal and the distal surface of the reagent zone. In certain embodiments, this is achieved by dispensing, pipetting, contactless ink jet printing, or a combination thereof. By adding an aqueous solution to the reagent zone, the stored reagent agent is released from the reagent zone and can enter the analyte capture zone. During analysis steps, when the capture layer is attached to a rigid support (300, described below), the directed movement/ convection of the reagent is controlled by applying a vacuum to the proximal side of the analyte capture zone. The control of the vacuum over time ensures incubation (no vacuum, only capillary force) and the efficient transport of reagents (increased vacuum between 0 and −500 mbar) from the reagent zone to the analyte capture zone and the analytes comprised therein. The vacuum and the resulting directed movement of reagents thus decreases incubation times and increases the sensitivity of analyte detection using the patch according to the invention.

In a typical example, after analyte collection, the analyte capture zone (105) of the capture layer (100) comprises an analyte. Subsequently, the analyte is contacted with the different reagents comprised in the reagent zone (205) of the analysis cover layers (200 P2, P3; ... Pn). The reagents may interact with the analyte, e.g. by direct or indirect binding, or they may otherwise be advantageous for the detection of the analyte, e.g by adjusting the pH, impeding unspecific binding, preventing contamination or stabilizing the analyte.

A reagent that is especially useful during analyte collection, when the patch is attached to a patient's skin, is a surfactant or detergent. In the context of the present specification, the term "surfactant" relates to a compound capable of lowering the surface tension between two liquids or between a liquid and a solid. Surfactants may be anionic, cationic, zwitterionic, non-ionic or combinations thereof. Surfactants that are advantageous for the method according to the invention help to increase the extraction of analytes from the skin, while maintaining the structure and functionality of the extracted analytes.

Non-limiting examples of surfactants are sodium lauryl sulfate (SLS), 3-(decyl dimethyl ammonio) propane sulfonate, polyethylene glycol dodecyl ether, poloxamers sodium laureth sulfate (SLA), sodium tridecyl phosphate (TDP), sodium deoxycholate (SDC), sodium decanoyl sarcosinate (NDS), sodium lauroyl sarcosinate (NLS), sodium palmitoyl sarcosinate (NPS), octyl trimethyl ammonium chloride (OTAB), dodecyl trimethyl ammonium chloride (DDTAB), tetradecyl trimethyl ammonium chloride (TTAB), dioctyl sodium sulfosuccinate, 3-[(3-Cholamidopropyl) dimethyl ammonio]1-propane sulfonate (CHAPS), 3-(Decyl dimethyl ammonio) propane sulfonate (DPS), 3-(Dodecyl dimethyl ammonio) propane sulfonate (DDPS), polyethylene glycol dodecyl ether (B30), polyoxyethylene 23-lauryl ether (B35), polyoxyethylene 10-cetyl ether (B56), polyoxyethylene 2-stearyl ether (B72), polyethylene glycol oleyl ether (B93), nonylphenol polyethylene glycol ether (NP9).

In certain embodiments, the proximal surface (101) of the capture layer (100), in particular the proximal surface (101) of the analyte capture zone (105) is sealed with a removable cover (401). By way of non-limiting example, this removable cover is a protective foil. The removable cover (401) serves as a barrier protecting the analyte capture zone (105) from dust, dirt, scales, blood cells, blood clots, bacteria, fungi, and other particles. Such particles might otherwise interact with the capture process, and especially with the detection (optical and electrical) of the analyte. In certain embodiments, the removable cover (401) is divided in areas that can be removed separately. In some of these instances, each area of the removable cover (401) seals a single capture division (106) or a subgroup of capture divisions. In some instances, a first area of the removable cover (401) seals the entire analyte capture zone (105). This area of the removable cover is attached to a narrow portion of the fastener zone that borders to the analyte capture zone. A second area of the removable cover (401) seals the fastener zone (104).

In certain embodiments, the proximal surface (101) of the capture layer (100) is attached to a rigid support (300). The rigid support (300) has a proximal surface (301) and a distal surface (302). The rigid support (300) comprises a fastener zone (304) and a central opening (305). In certain embodiments, the rigid support (300) comprises more than one central opening (305). In certain embodiments, the rigid support (300) comprises 2-8 central openings (305). The proximal surface (101) of the capture layer (100) is attached to the fastener zone (304) of the rigid support (300). The central opening (305) of the rigid support (300) is aligned with the analyte capture zone (105) of the capture layer (100). In instances where a cover layer (200) comprising a reagent zone (205) is attached to the capture layer, the central opening (305) of the rigid support (300) is also aligned with the reagent zone (205) of the cover layer (200).

By way of non-limiting example, the rigid support (300) is made of polycarbonate, polypropylene, polystyrol, polyethylene terephthalate (PET) or glass. In certain embodiments, it has a thickness of 0.2-2 mm.

The rigid support (300) allows to have a thin and flexible capture layer (100), which is important when the patch is attached to curved surfaces such as skin surfaces, and has to conform well with the latter. On the other hand, during the analysis phase, when the capture layer (100) is attached to the rigid support (300), the rigid support (300) gives it rigidness and mechanical stability for handling. One handling step during which stability of the stack is especially important are the application of liquids to the reagent zone (205). This can be done with or without hydrostatic pressure or with back pressure of a gas volume. Another handling step during which stability of the stack is important is the extraction of liquids via the central opening(s) (305) of the rigid support (300) or via the reagent zone (205). In instances where a liquid is extracted via the central opening(s) (305) of the rigid support (300), a vacuum is applied to the central opening(s) (305). The advantages of the vacuum application and the resulting directed movement of reagents have been described above.

In instances where a liquid is extracted via the reagent zone, an adaptor (501) can be used to connect the reagent zone (205) to a confined volume, particularly to a syringe. By pulling the plunger of the syringe, the liquid is moved from the analyte capture zone to the reagent zone and subsequently extracted from there. Alternatively, liquid may be extracted via the reagent zone through capillary force, in particular by placing an absorbent material (e.g. cellulose) above the reagent zone, or by a vacuum applied to the reagent zone.

Stability of the stack is also important when one cover layer (200) is removed from the capture layer (100) and another cover layer (200) is attached to the capture layer (100). The rigid support (300) allows successive precise alignment of the capture layer (300) with several different cover layers (200). On the rigid support (300), capture layer (100) and cover layer can be taken apart and re-assembled at least 5 times. They still retain their structural properties. The fastener zones (104, 204) are still delimited by water impermeable barrier zones (108, 208) from analyte capture zone (105) and reagent zone (205), respectively. The capture divisions (106) stay isolated from each other. The reagent divisions stay (206) isolated from each other. In other words, there is no leakage between the layers of the patch or between the single divisions (106, 206) within one layer.

In certain embodiments, the rigid support (300) comprises vacuum openings (306) designed to apply a vacuum to the proximal surface (101) of the capture layer (100). In certain embodiments, the vacuum openings (306) are comprised in the fastener zone (304) of the rigid support (300).

In the analyte detection method using the patch according to the invention, a vacuum is applied to the proximal surface of the rigid support (300) at two distinct time points and for two distinct purposes:
 1. First vacuum: directed movement of reagents from the reagent zone (205) to the analyte capture zone (105) (and subsequently from there into an absorber pad (402) proximal to the analyte capture zone). In certain embodiments, a vacuum of 0 to −400 mbar is applied for this purpose.
 2. Second vacuum: fixation of the capture layer to the rigid support (300) during removal of cover layer from capture layer. In certain embodiments, a vacuum of −50 to −500 mbar is applied for this purpose.

The capture layer (100) is fixed to the rigid support (300) on the one hand by vacuum applied via the vacuum openings (306) and on the other hand by the adhesive (133) on the proximal surface of the fastener zone (104) of the capture layer (100). When a cover layer (200) is removed from the capture layer (100), the capture layer (100) stays fixed on the rigid support (300). This is due to the fact that the adhesive force between rigid support and capture layer (vacuum and adhesive) is stronger than the adhesive force between capture layer (100) and cover layer (adhesive only).

In certain embodiments, the capture layer (100), the cover layer (200) and the rigid support (300) each comprise registration holes (103, 203, 303) for aligning the layers by pins (403). In certain embodiments, each layer comprises at least 2 registration holes. In certain embodiments, each layer comprises 2 to 4 registration holes. In certain embodiments, each layer comprises 4 registration holes. During alignment, the pins (403) are inserted in the registration holes (103, 203, 303). The skilled person is aware that the registration holes can be replaced by notches in the rim of capture layer (100), cover layer (200) and the rigid support (300).

In certain embodiments, the rigid support (300) comprises no registration holes, but pins (403) for aligning capture layer (100) and the cover layer (200) on the rigid support (300).

In certain embodiments, the capture layer (100) and the cover layer (200) each comprise
  a. an adherence layer (130, 230) comprising the described adhesive (133, 233) capable of removably fastening capture layer to surface or cover layer to capture layer;
  b. a reactive layer (110, 210) and
  c. optionally a reinforcement layer (120, 220).

The reactive layer (110) of the capture layer (100) comprises the analyte capture zone (105). In instances where the cover layer (200) comprises a reagent zone (205), the reagent zone is comprised in the reactive layer (210) of the cover layer (200). The purpose of the reinforcement layer is to stabilize the capture layer (100) or cover layer (200). Stabilization is especially important for the capture layer (100), particularly in instances where the first water permeable material is nitrocellulose or a polyester non-woven backed nitrocelllulose. Stability of the cover layer is particularly important during the process of attaching the cover layer (100) to and removing it from a surface (during analyte collection) or the rigid support (300). The reinforcement layer (120, 220) comprises a high-tack adhesive on its distal side, which fixes the reinforcement layer (120, 220) permanently to the reactive layer (110, 210).

By way of non-limiting example, the reinforcement layer (120, 220) consists of polyester, in particular polyethylene terephthalate (PET).

By way of non-limiting example, the adherence layer (130, 230) consists of a polyurethane, in particular a thermoplastic polyurethane (TPU).

In certain embodiments, the order of the layers from proximal to distal is: adherence layer (130, 230), reinforcement layer (120, 220), reactive layer (110, 210) (FIGS. 2-5). In other words, the reinforcement layer is located between the adherence layer and the reactive layer. In these instances, the adherence layer (130, 230) comprises a low tack adhesive on its proximal side and a high tack adhesive on its distal side. The high tack adhesive (135, 235) on the distal side fixes the adherence layer (130, 230) permanently to the reinforcement layer (120, 220). The high tack adhesive on the distal side of the reinforcement layer (120, 220) fixes reinforcement layer (120, 220) permanently to the reactive layer (110, 210). The low-tack adhesive corresponds to the above-mentioned adhesive (133, 233) ensuring removable attachment. The low tack adhesive on the proximal side of the adherence layer (130) of the capture layer (100) can fix the capture layer removably to a surface during analyte collection or to the rigid support (300) during the analysis steps. The low tack adhesive on the proximal side of the adherence layer (230) of the cover layer (200) can fix the cover layer removably to the capture layer.

In certain embodiments, the adherence layer (130, 230) is smaller in size (smaller circumference) than the reinforcement layers (120, 220) and the reactive layers (110, 210) leaving a zone on the rim of the patch free from adhesives. This can facilitate the removal and attachment of capture layer (100) to rigid support (300), and cover layer (200) to capture layer (100).

In an alternative embodiment, the order of the layers from proximal to distal is: adherence layer (130, 230), reactive layer (110, 210), reinforcement layer (120, 220) (FIG. 10, 11A).

In certain embodiments, capture layer (100) and cover layer (200) each comprise an adherence layer (130, 230) and a reactive layer (110, 210), but no reinforcement layer (120, 220). In certain embodiments, the adherence layer (130, 230) comprises a medium-tack adhesive on its proximal side and no adhesive on its distal side. In these instances, the adherence layer (130, 230) is larger in size (bigger circumference) than the reactive layer (110, 210) and is located distal to the reactive layer. The medium-tack adhesive on the proximal side of the adherence layer (130) serves two purposes:
  1. Stability within the capture/cover layer: reactive layer is fixed to adherence layer.
  2. Reversible attachment of capture layer to surface, respectively of cover layer to capture layer.

In certain embodiments, the first water permeable material comprises nitrocellulose. In certain embodiments, the first water permeable material is nitrocellulose. In certain embodiments, the first water permeable material is nitrocellulose backed with a water permeable stabilizing layer, in particular a polyester non-woven layer, glass fiber layer, cellulose layer or other porous polymer layer. In certain embodiments, the second water permeable material is selected from glass fiber, cotton, nonwoven polyester, and cellulose or any other material able to retain a reagent until it is dissolved away by a buffer. In certain embodiments, the second water permeable material is selected from glass fiber and cellulose.

In certain embodiments, the first divider (107), the second divider (109) and/or the reagent divider (207) comprise a layer of hydrophobic material introduced in the reactive layer (110, 210), wherein in particular said hydrophobic material extends from the proximal surface (101, 201) to the distal surface (102, 202) of the reactive layer (110, 210).

In certain embodiments, the second divider (109) and/or the reagent divider (207) are formed by
  a. a layer of hydrophobic material introduced in the reactive layer (110, 210), wherein in particular the hydrophobic material extends from the proximal surface (101, 201) to the distal surface (102, 202) of the reactive layer (110, 210): second divider/reagent divider in reactive layer (119/217),
  b. the adherence layer (130, 230), in particular thermoplastic polyurethane (TPU) and the adhesives comprised on the adherence layer: second divider/reagent divider in adherence layer (139/237),
  c. optionally the reinforcement layer (120, 220), in particular polyethylene terephthalate (PET) and the adhesives comprised on the reinforcement layer: second divider/reagent divider in reinforcement layer (129/227).

The second divider in the adherence layer (139) comprises the high and low tack adhesives comprised on the adherence layer (130): 133, 135.

The second divider in the reinforcement layer (129) comprises the adhesives comprised on the reinforcement layer (120).

The reagent divider in the adherence layer (237) comprises the high and low tack adhesives comprised on the adherence layer (230): 233, 235.

The reagent divider in the reinforcement layer (227) comprises the adhesives comprised on the reinforcement layer (220).

The adhesives provide for sufficient sealing between the individual layers of the dividers.

In certain embodiments, a capture division (106) and a reagent division (206) are in fluid connection at the interface of the proximal surface (101) of the capture layer (100) and the distal surface (202) of the cover layer (200). The capture division (106) and the reagent division (206) in fluid connection are sealed from the surrounding area and from all other capture divisions and all other reagent divisions by a water impermeable barrier comprising the first divider (107) and the reagent divider (207). One reagent division (206) may be in fluid connection with more than one capture division (106). One capture division (106) may be in fluid connection with more than one reagent division (206).

During the analysis steps following analyte collection, the capture layer (100) is attached to the rigid support (300). The cover layer used during analyte collection (200 P1) or another cover layer (200 Pn) is attached to the capture layer (100). As described above, optionally, a syringe or pipette containing an aqueous solution can be attached to the reagent zone (206) of the cover layer (200) via an adapter (501). By pressing the plunger of the syringe or pipette to an intermediate position, the aqueous solution can be transferred from the syringe or pipette via the reagent divisions (206), where it releases the reagent, to the capture divisions (106). By pressing the plunger of the syringe or pipette beyond said intermediate position, the aqueous solution can be transferred via the central opening (305) of the rigid support (300) to an absorbent pad (402) below the rigid support (300).

In certain embodiments, the planar cover layer is impermeable to water. In these instances, the cover layer forms a complete occlusion. Such embodiments can be advantageous during analyte collection, but are not suitable for analysis steps. In instances where a cover layer that is impermeable to water is used during analyte collection, analytes are extracted by incubation performed with water transpired from the surface and captured in the occlusion. This alternative analyte collection method is particularly relevant in instances where the surface is skin. In certain embodiments of the patch according to the invention, the patch is configured as a patch for multiplex detection of analytes. In other words, using the patch according to the invention, it is possible to simultaneously detect more than one analyte using a single patch. In certain embodiments, it is possible to simultaneously detect more than five different analytes using a single patch.

In certain embodiments of the patch according to the invention, the patch is configured as a patch for detection of analytes on human or animal skin.

In certain embodiments of the patch according to the invention, the patch is configured as a patch for detection of analytes by an immunological method.

In certain embodiments of the patch according to the invention, the patch is configured as a diagnostic patch. In other words, the use of the patch enables or supports a diagnosis to be made, in particular the diagnosis of a dermatological condition or infection.

According to a second aspect, a patch assembly kit is provided. The patch assembly kit comprises a capture layer (100), a sampling cover layer (200 P1), one or several analysis cover layers (200 Pn) and a rigid support (300).

a. The capture layer (100) has a proximal surface (101) and a distal surface (102). In instances where the planar patch is applied to a surface for analyte collection, the proximal surface (101) of the capture layer (100) faces towards this surface and the distal surface (102) of the capture layer (100) faces away from it.

The capture layer (100) is characterized by a thickness of 10 μm to 2 mm. In certain embodiments, the capture layer (100) is characterized by a thickness of to 25 μm to 1 mm. In certain embodiments, the capture layer (100) is characterized by a thickness of 50 μm to 500 μm. In certain embodiments, the capture layer (100) is characterized by a thickness of approximately 200 μm.

The capture layer (100) comprises an analyte capture zone (105) and a fastener zone (104).

i. The analyte capture zone (105) extends from the proximal surface (101) to the distal surface (102). The analyte capture zone (105) consists of a first water permeable material. In certain embodiments, the first water permeable material is capable of transporting an aqueous solution. In certain embodiments, the first water permeable material is capable of transporting an aqueous solution by capillary force. In certain embodiments, the first water permeable material is nitrocellulose, or polyester non-woven backed nitrocellulose. The first water permeable material comprises a ligand capable of binding specifically to an analyte. Binding between ligand and analyte primarily takes place close to the proximal or distal surface of the capture zone (105).

ii. The fastener zone (104) is impermeable to water and/or delimited from said analyte capture zone by a water impermeable barrier zone (108). In certain embodiments, the water impermeable barrier zone (108) is composed of a hydrophobic material selected from the group comprising a wax, a thermoplastic polymer, a thermoplastic copolymer, in particular thermoplastic polyurethane, an epoxy, and an adhesive. The fastener zone (104) comprises, on the proximal surface (101), an adhesive (133) capable of fastening the capture layer (100) removably to a surface.

b. The sampling cover layer (200 P1) has a proximal surface (201) and a distal surface (202). The sampling cover layer (200 P1) is characterized by a thickness of 10 μm to 3 mm. In certain embodiments, the sampling cover layer (200 P1) is characterized by a thickness of to 25 μm to 1 mm. In certain embodiments, the sampling cover layer (200 P1) is characterized by a thickness of 50 μm to 500 μm. In certain embodiments, the sampling cover layer (200 P1) is characterized by a thickness of approximately 400 μm. The sampling cover layer comprises, on the proximal surface (201), an adhesive (233) capable of fastening the sampling cover layer (200 P1) removably to the distal surface (102) of the capture layer (100).

c. The analysis cover layers (200 Pn) have a proximal surface (201) and a distal surface (202). The analysis cover layers (200 Pn) comprise a reagent zone (205) and a fastener zone (204).

i. The reagent zone (205) extends from the proximal surface (201) to the distal surface (202). The reagent zone (205) consists of a second water permeable material. In certain embodiments, the second water permeable material is capable of transporting an aqueous solution. In certain embodiments, the second water permeable material is capable of transporting an aqueous solution by capillary force.

ii. The fastener zone (204) is impermeable to water and/or delimited from the reagent zone (205) by a water impermeable barrier zone (208). In certain embodiments, the water impermeable barrier zone (208) is composed of a hydrophobic material selected from the group comprising a wax, a thermoplastic polymer, a thermoplastic copolymer, in particular thermoplastic polyurethane, an epoxy, and an adhesive. The fastener zone (204) comprises, on the proximal surface (201), an adhesive (233) capable of fastening the sampling cover layer (200) removably to the distal surface (102) of the capture layer (100).

d. The rigid support (300) has a proximal surface (301) and a distal surface (302). The rigid support (300) comprises a fastener zone (304) and a central opening (305). In certain embodiments, the rigid support (300) comprises more than one central opening (305). In certain embodiments, the rigid support (300) comprises 2-8 central openings (305). The proximal surface (101) of the capture layer (100) is to be attached to the fastener zone (304) of the rigid support (300). The central opening (305) of the rigid support (300) is to be aligned with the analyte capture zone (105) of the capture layer (100) and the reagent zone (205) of the analysis cover layer (200). In certain embodiments, the rigid support (300) comprises vacuum openings (306) designed to apply a vacuum to said proximal surface (101) of said capture layer (100).

The patch assembly kit also comprises one or several buffers suitable for use with the patch, in particular for extraction of analytes from the skin and for releasing reagents stored in the reagent zone (205).

In certain embodiments of this aspect of the invention, the sampling cover layer (200 P1) comprises a reagent zone (205 P1) and a fastener zone (204 P1).

a. The reagent zone (205 P1) extends from the proximal surface (201 P1) to the distal surface (202 P1). The reagent zone (205 P1) consists of a second water permeable material.

b. The fastener zone (204 P1) is impermeable to water and/or delimited from said reagent zone (205 P1) by a water impermeable barrier zone (208 P1).

In certain embodiments of this aspect of the invention, the analyte capture zone (105) is compartmentalized into a plurality of confined water permeable capture divisions (106). Each capture division comprises the ligand capable of binding specifically to an analyte. In certain embodiments, the analyte capture zone (105) is compartmentalized into 1-1000 capture divisions (106). In certain embodiments, the analyte capture zone (105) is compartmentalized into 1-256 capture divisions (106). Each capture division is separated from any other capture division by a first divider (107) that is impermeable to water.

In certain embodiments of this aspect of the invention, the reagent zone (205) is compartmentalized into a plurality of confined water permeable reagent divisions (206). In certain embodiments, the reagent zone (205) is compartmentalized into 1-144 reagent divisions (206). In certain embodiments, the reagent zone (205) is compartmentalized into 1-64 reagent divisions (206). In certain embodiments, the reagent zone (205) is compartmentalized into 1-36 reagent divisions (206). In certain embodiments, the reagent zone (205) is compartmentalized into 1-16 reagent divisions (206). Each reagent division is separated from any other reagent division by a reagent divider (207) that is impermeable to water.

In certain embodiments of this aspect of the invention, the reagent divisions (206) comprise a reagent. The reagent may be in dried, lyophilized, gel or aqueous form. In certain embodiments, the reagent is selected from the group comprising an acid, a base, a salt, a sugar, a surfactant, a protein, a nucleic acid, an antimicrobial agent, in particular an antibacterial and/or an antifungal agent, a dye (organic, inorganic, and solid state), a fluorophore, lanthanides, upconverting phosphor nanoparticles, colloidal gold, cellulose nanobeads, latex, a reagent for total protein quantification, an affinity molecule, in particular an antibody (primary or secondary), an aptamer, an enzyme, a molecularly imprinted polymer, a ionophore, a pore or motor protein for nucleic acid sequencing, a nanoparticle and a microbead. In certain embodiments, the reagents are immobilised on microbeads and nanoparticles. In certain embodiments, the reagent divisions (206) comprise a reagent selected from an acid, a base, a salt, a sugar, a surfactant, a protein, a fluorophore, an upconverting phosphor nanoparticle, colloidal gold, a reagent for total protein quantification and an antibody. In certain embodiments, the reagent divisions (206) comprise a primary antibody and a fluorophore. In certain embodiments, the reagent divisions (206) comprise a primary antibody, a secondary antibody and a fluorophore. In certain embodiments, the reagent divisions (206) comprise a primary antibody and/or a secondary antibody, a fluorophore, an ionic buffer, particularly a phosphate buffer, a sugar, particularly trehalose and/or sucrose, a surfactant, particularly poly vinyl pyrrolidone (PVP), and a blocking reagent, particularly bovine serum albumin (BSA).

In certain embodiments of this aspect of the invention, the sampling cover layer (200 P1) is impermeable to water.

According to another aspect, a diagnostic method is provided. The method comprises the following steps:

a. A flexible planar patch is provided. The planar patch comprises a capture layer (100) and a sampling cover layer (200 P1). The capture layer (100) comprises an analyte capture zone (105) comprising an analyte.

b. Providing a rigid support (300) and attaching the planar patch to the rigid support.

c. Optionally, an aqueous solution is applied to the reagent zone (205 P1) followed by an incubation time of between 1-5 seconds up to one hour, and a first vacuum is applied to the proximal surface (101) of the capture layer (100).

d. A second vacuum is applied to the proximal surface (101) of the capture layer (100). Simultaneously, the sampling cover layer (200 P1) is removed from the capture layer (100).

e. An analysis cover layer (200 P2) comprising a reagent zone (205 P2) is attached to the capture layer (100).

f. An aqueous solution is applied to the reagent zone (205 P2), followed by an incubation time of between 1-5 seconds up to one hour, and a first vacuum is applied to the proximal surface (101) of the capture layer (100).

g. A second vacuum is applied to the proximal surface (101) of the capture layer (100). Simultaneously, the analysis cover layer (200 P2) is removed from the capture layer (100).

h. Optionally, steps d to f are repeated 1 to 5 times using analysis cover layers (200 P3-P7).

i. The analyte comprised in the analyte capture zone (105) is detected.

Step a: The flexible planar patch provided in step a) is suitable for application to a patient's skin or mucous membrane. It comprises a capture layer (100) and a sampling cover layer (200 P1).

i. The capture layer (100) has a proximal surface (101) and a distal surface (102). The capture layer (100) comprises an analyte capture zone (105) and a fastener zone (104).

1. The analyte capture zone (105) extends from the proximal surface (101) to said distal surface (102). The analyte capture zone (105) consists of a first water permeable material. In certain embodiments, the first water permeable material is capable of transporting an aqueous solution. In certain embodiments, the first water permeable material is capable of transporting an aqueous solution by capillary force. In certain embodiments, the first water permeable material is nitrocellulose, or polyester nonwoven backed nitrocellulose. The first water permeable material comprises a ligand capable of binding specifically to an analyte.

2. The fastener zone (104) is impermeable to water and/or delimited from said analyte capture zone by a water impermeable barrier zone (108). In certain embodiments, the water impermeable barrier zone (108) is composed of a hydrophobic material selected from the group comprising a wax, a thermoplastic polymer, a thermoplastic copolymer, in particular thermoplastic polyurethane, an epoxy, and an adhesive. The fastener zone (104) comprises, on the proximal surface (101), an adhesive (133) capable of fastening the capture layer (100) removably to a surface.

ii. The sampling cover layer (200 P1) has a proximal surface (201 P1) and a distal surface (202 P2). The sampling cover layer comprises, on the proximal surface (201), an adhesive (233) capable of fastening the cover layer (200) removably to the distal surface (102) of the capture layer (100).

The analyte comprised in the analyte capture zone may be comprised on the proximal surface (101) of the analyte capture zone (105) or on the distal surface (102) of the analyte capture zone (105). In instances where the analyte is a microorganism, it will be comprised on the proximal side. In instances where the analyte is a biomolecule, it will be comprised on the distal side. The analyte capture zone serves thus as a filter, filtering the analytes according to their size.

Step b: The rigid support (300) has a proximal surface (301) and a distal surface (302). The rigid support (300) comprises a fastener zone (304) and a central opening (305). In certain embodiments, the rigid support (300) comprises more than one central opening (305). In certain embodiments, the rigid support (300) comprises 2-8 central openings (305). The proximal surface (101) of the capture layer (100) is attached to the fastener zone (304) of the rigid support (300). The central opening (305) of the rigid support (300) is aligned with the analyte capture zone (105) of the capture layer (100). The capture layer (100), the sampling cover layer (200 P1) and the rigid support (300) each comprise registration holes (103, 203, 303). Pins (403) are inserted in the registration holes (303) of the rigid support (300). When the planar patch is attached to the rigid support (300), the pins are also inserted into the registration holes (103, 203) of the capture layer (100) and the sampling cover layer (200 P1). This results in accurate alignment of patch and rigid support (300). In certain embodiments, the rigid support (300) also comprises vacuum openings (306) designed to apply a vacuum to the proximal surface (101) of the capture layer (100), thereby fixing the capture layer (100) to the rigid support (300). The planar patch is attached to the distal surface of the rigid support.

Step c: This optional step increases the amount of analytes bound to the analyte capture zone. In certain embodiments, the first vacuum is characterized by 0 to −400 mbar.

Step d: A second vacuum is applied to the capture layer (100). In certain embodiments, the second vacuum is characterized by −50 to −500 mbar. The capture layer (100) is thus fixed to the rigid support (300) on the one hand by vacuum applied via the vacuum openings (306) and on the other hand by the adhesive (133) on the proximal surface of the fastener zone (104) of the capture layer (100). When the sampling cover layer (200 P1) is removed from the capture layer (100), the capture layer (100) stays fixed on the rigid support (300). This is due to the fact that the adhesive force between rigid support and capture layer (vacuum and adhesive) is stronger than the adhesive force between capture layer (100) and sampling cover layer (adhesive only).

At this point, optionally, additional aqueous solution can be applied to the analyte capture zone (105) and be removed by vacuum.

Step e: The proximal surface (201) of the analysis cover layer (200 P2) is attached to the distal surface (102) of the capture layer (100). The analysis cover layer (200 P2) is aligned with the capture layer (100) and the rigid support (300) via registration holes (203) present in the analysis cover layer (200 P2) and the pins (403). The analysis cover layer (200 P2) has a proximal surface (201) and a distal surface (202). The analysis cover layer (200 P2) comprises a reagent zone (205) and a fastener zone (204).

i. The reagent zone (205) extends from the proximal surface (201) to the distal surface (202). The reagent zone (205) consists of a second water permeable material. In certain embodiments, the second water permeable material is capable of transporting an aqueous solution. In certain embodiments, the second water permeable material is capable of transporting an aqueous solution by capillary force. The reagent zone comprises a reagent. The reagent may be in dried, lyophilized, gel or aqueous form. In certain embodiments, the reagent is selected from the group comprising an acid, a base, a salt, a sugar, a surfactant, a protein, a nucleic acid, an antimicrobial agent, in particular an antibacterial and/or an antifungal agent, a dye (organic, inorganic, and solid state), a fluorophore, lanthanides, upconverting phosphor nanoparticles, colloidal gold, cellulose nanobeads, latex, a reagent for total protein quantification, an affinity molecule, in particular an antibody (primary or secondary), an aptamer, an enzyme, a molecularly imprinted polymer, a ionophore, a pore or motor protein for nucleic acid sequencing, a nanoparticle and a microbead. In certain embodiments, the reagents are immobilised on microbeads and nanoparticles. In certain embodiments, the reagent divisions (206) comprise a reagent selected from an acid, a base, a salt, a sugar, a surfactant, a protein, a fluorophore, an upconverting phosphor nanoparticle, colloidal gold, a reagent for total protein quantification and an antibody. In certain embodiments, the reagent divisions (206) comprise a primary antibody and a fluorophore. In certain embodiments, the reagent divisions (206) comprise a primary antibody, a secondary antibody and a fluorophore. In certain embodiments, the reagent divisions (206) comprise a primary antibody and/or a secondary antibody, a fluorophore, an ionic buffer, particularly a phosphate buffer, a sugar, particularly trehalose and/or sucrose, a surfactant, particularly poly vinyl pyrrolidone (PVP), and a blocking reagent, particularly bovine serum albumin (BSA).The reagent zone (205) is aligned with the analyte capture zone (105) of the capture layer (100) and the central opening (305) of the rigid support (300).

ii. The fastener zone (204) is impermeable to water and/or delimited from said reagent zone (205) by a water impermeable barrier zone (208). In certain embodiments, the water impermeable barrier zone (208) is composed of a hydrophobic material selected from the group comprising a wax, a thermoplastic polymer, a thermoplastic copolymer, in particular thermoplastic polyurethane, an epoxy, and an adhesive. The fastener zone (204) comprises, on its proximal surface (201), an adhesive (233) capable of fastening the analysis cover layer (200) removably to the distal surface (102) of the capture layer (100).

Step f: An aqueous solution is applied to the reagent zone (205), followed by an incubation time of between 1-5 seconds up to one hour, and a first vacuum is applied to the proximal surface (101) of the capture layer (100). In certain embodiments, the first vacuum is characterized by 0 to −400 mbar. This results in the direction of the aqueous solution from the reagent zone (205) via the analyte capture zone (105) to a liquid reservoir/absorber pad (402) below the central opening (305). In the reagent zone, the aqueous solution releases the stored reagent and transports it to the analytes comprised in the analyte capture zone. In certain embodiments, 1-1000 µl of aqueous solution are applied. In certain embodiments, 5-500 µl of aqueous solution are applied. In certain embodiments, 10-100 µl of aqueous solution are applied. The skilled person is aware that in instances where the reagent comprised in the reagent layer is present in dried or lyophilized form, the amount of aqueous solution that has to be added to the reagent zone in order to release the stored agent is higher than in instances where the reagent is stored in gel form or aqueous form.

Step g: A second vacuum is applied to the capture layer (100). In certain embodiments, the second vacuum is characterized by −50 to −500 mbar. The capture layer (100) is thus fixed to the rigid support (300) on the one hand by vacuum applied via the vacuum openings (306) and on the other hand by the adhesive (133) on the proximal surface of the fastener zone (104) of the capture layer (100). When the analysis cover layer (200 P2) is removed from the capture layer (100), the capture layer (100) stays fixed on the rigid support (300). This is again due to the fact that the attachment between rigid support (300) and capture layer (100) is stronger (vacuum and adhesive) than the attachment between capture layer (100) and analysis cover layer (200 P2) (adhesive only).

Step h: Optionally, steps e to g are repeated 1 to 5 times. Each time, a new analysis cover layer comprising new reagents is used. In certain embodiments, steps e to g are repeated 1 to 2 times. In some instances, e.g. when the first analysis cover layer (200 P2) contains labelled secondary antibodies, no repetition of steps e to g is needed.

Step i: The analyte comprised in the analyte capture zone (105) is detected. The capture layer (100) can be easily attached to and read on standard optical reader equipment (e.g. confocal laser scanning microscope or microarray reader).

In instances where the analyte has a diameter that is larger than the pore size of the first water permeable material of the analyte capture zone (105), and the proximal side of the analyte capture zone comprises a ligand specifically binding to said analyte, this analyte can be detected on the proximal side of the capture layer (101). In instances where the analyte has a diameter that is smaller than the pore size of the first water permeable material of the analyte capture zone (105), and the distal side of the capture zone comprises a ligand specifically binding to said analyte, this analyte can be detected on the distal side of the capture layer. In instances where of the capture zone comprises on its proximal side a ligand specifically binding to a first analyte with diameter larger than the pore size and on its distal side a ligand specifically binding to a second analyte with diameter smaller than the pore size, both analytes can be detected on the same capture layer: the first analyte on the proximal side and the second analyte on the distal side. This can be relevant for the simultaneous detection of a microorganism (first analyte) and the reaction of a patient towards this microorganism, e.g. in the form of secreted cytokines (second analyte).

In certain embodiments of this aspect of the invention, the analyte capture zone (105) is compartmentalized into a plurality of confined water permeable capture divisions (106) and the reagent zone (205) is compartmentalized into a plurality of confined water permeable reagent divisions (206). At the interface of the proximal surface (101) of the capture layer (100) and the distal surface (202) of the cover layer (200), a capture division (106) and a reagent division (206) are in fluid connection and sealed from the surrounding area by a water impermeable barrier. One reagent division (206) may be in fluid connection with more than one capture division (106). One capture division (106) may be in fluid connection with more than one reagent division (206). According to another aspect of the invention, a diagnostic method is provided. The method is conducted as described above with the following modifications:

Step a: This step comprises no modifications.

Step b: The rigid support (300) is inverted prior to attachment of the planar patch. The planar patch is attached to the proximal surface (301) of the rid support (300), instead of the distal surface (302).

Step c and d: These steps comprise no modifications.

Step e: In this additional step, the rigid support (300) is inverted (back to its "normal" position). This results in the inversion of the capture layer (100) attached to the rigid support (300). In other words, the originally distal surface (102) of the capture layer (100) is now oriented downwards.

Step f: The analysis cover layer (200 P2) is attached to the distal surface (302) of the rigid support (302), instead of the distal surface (102) of the capture layer (100). In other words, the rigid support (300) is located between the capture layer (100) and the analysis cover layer (200 P2).

Step g: During this immunofiltration step, the first vacuum is applied to the downwards oriented, originally distal surface (102) of the capture layer (100). The skilled person is aware that in order to ensure that reagent divisions (206) and capture divisions (106) are in fluid connection and sealed from the surrounding area by a water impermeable barrier, the rigid support has to comprise several central openings (305) which are aligned with reagent divisions (206) and capture divisions (106).

Step h: The analysis cover layer (200 P2) is removed from the distal surface (302) of the rigid support (302).

Step i: Steps f to h are repeated (optionally).

Step L: Detection of the analyte as described above.

In certain embodiments of this aspect of the invention, step i (respectively step j, in instances where the rigid support is inverted and the analysis cover layer (200 P2) is attached to the rigid support instead of the capture layer) comprises detecting said analyte by a detection method selected from electrical detection, magnetic field detection, thermal detection and optical detection, more particularly by a detection method selected from impedance spectroscopy, voltammetry, ISFET-based detection, magnetic field sensor, thermal contrast measurement (Quin et al., Angew Chem Int Ed Engl. 2012 Apr. 27; 51(18): 4358-4361), colour and optical absorption change, luminescence (including fluorescence and chemiluminescence) or turbidity measurement. In instances where the detection method is electrical or thermal—in case wired temperature sensors are used for the latter—the capture layer comprises electrical leads and contacts to connect electrodes and electronic integrated circuits, embedded in or on the membrane materials.

In certain embodiments of this aspect of the invention, analyte comprised in said analyte capture zone (105) has been obtained from a patient's skin or mucous membrane.

In certain embodiments of this aspect of the invention, the diagnostic method comprises attaching the patch to a patient's skin or mucous membrane prior to step a. In this step, analytes present on the skin or mucous membrane are transferred to the analyte capture zone (105). In certain embodiments, an aqueous solution is applied to the reagent zones (205) comprised in the sampling cover layer (200) of the patch during this analyte collection step.

For collection of analytes, the flexible planar patch can also be used as a swab. In these instances, the capture layer is sealed by a removable cover (401) that is divided in areas that can be removed separately. First, the part of the removable cover (401) that seals the analyte capture zone (105) is removed. Then the patch is wiped over a surface to be analyzed, wherein the now exposed analyte capture zone (105) faces towards the surface. Subsequently, the part of the removable cover (401) that seals the fastener zone (104) is removed, exposing the adhesive (133) on the fastener zone (104). Now the patch is mounted on the rigid support (300) for further analysis of the analytes as described in detail below. One exemplary application for the use of the patch as a swab during analyte collection is the detection of vaginal mycosis.

Collection of analytes can also be conducted while the flexible planar patch or the capture layer (100) of the patch assembly kit is attached to the rigid support (300). A vacuum pump can be used to draw air through the analyte capture zone (105) (and through the reagent zone (104) in instances where a cover layer (200) is attached), resulting in the transfer of analytes present in the air to the analyte capture zone (105). If the air comprises larger particles that are either not relevant for analysis or not suitable for analysis using the patch, these can be filtered out by using a size-selective filter placed in front of the analyte capture zone. In an analogous way, analytes present in solutions (e.g. water samples) or dispersions (e.g. of soil samples) can be analyzed.

Wherever alternatives for single separable features are laid out herein as "embodiments", it is to be understood that such alternatives may be combined freely to form discrete embodiments of the invention disclosed herein.

The invention is further illustrated by the following examples, figures and items, from which further embodiments and advantages can be drawn. These examples are meant to illustrate the invention but not to limit its scope.

Figure 1:
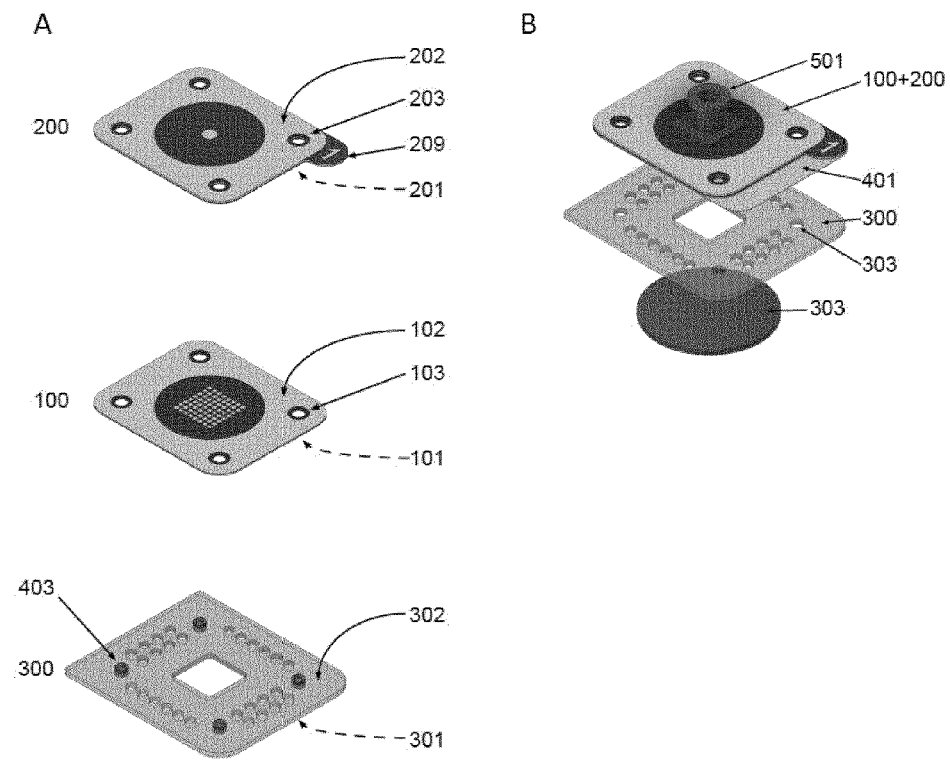
FIG. 1A shows capture layer (100), cover layer (200) and rigid support (300). The curved arrows point to the distal surface (102, 202, 302) of each layer. The curved, dashed arrows point to the proximal surface (101, 201, 301) of each layer. The registration holes in cover layer and capture layer (103, 203) are indicated. The cover layer comprises a tab (209) for easy removal. The rigid support optionally comprises pins (403) for alignment of the three layers.
In FIG. 1B, the cover layer (200) is shown attached to the capture layer (200). Additional elements shown: absorber pad (402), removable cover (401) attached to the proximal surface of the capture layer and adapter (501) attached to the cover layer. The rigid support comprises registration holes (303) instead of the alignment pins, which in this case are provided by the analysis stage to which layers are mounted.
Figure 2:
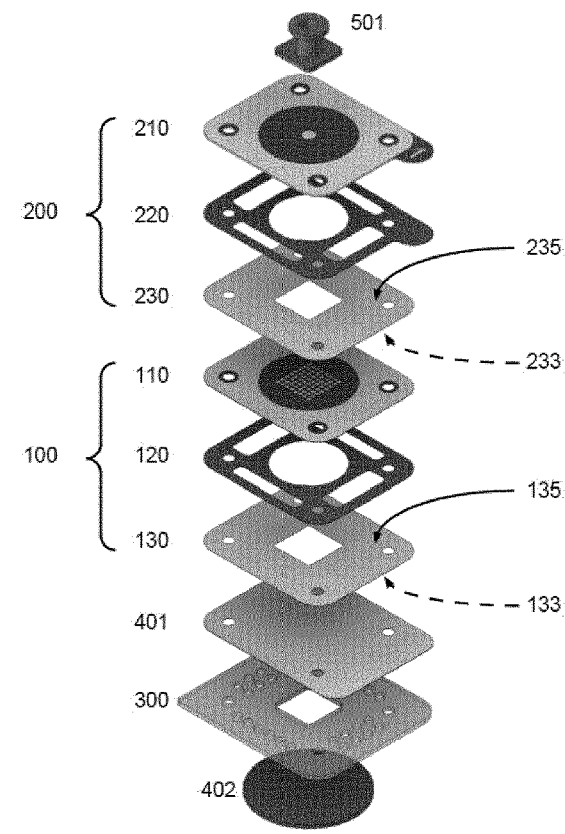
FIG. 2 shows an exploded view of capture layer (100) and cover layer (200). Reactive layers (110, 210), reinforcement layers (120, 220) and adherence layers (130,230) are indicated. At the adherence layers (130, 230), the curved arrows point to the distal surfaces, which comprise a high tack adhesive (135, 235) and the curved, dashed arrows point to the proximal surfaces (130, 230), which comprise a low tack adhesive (133, 233). An adapter (501) can be attached to the cover layer (200).
Figure 3:
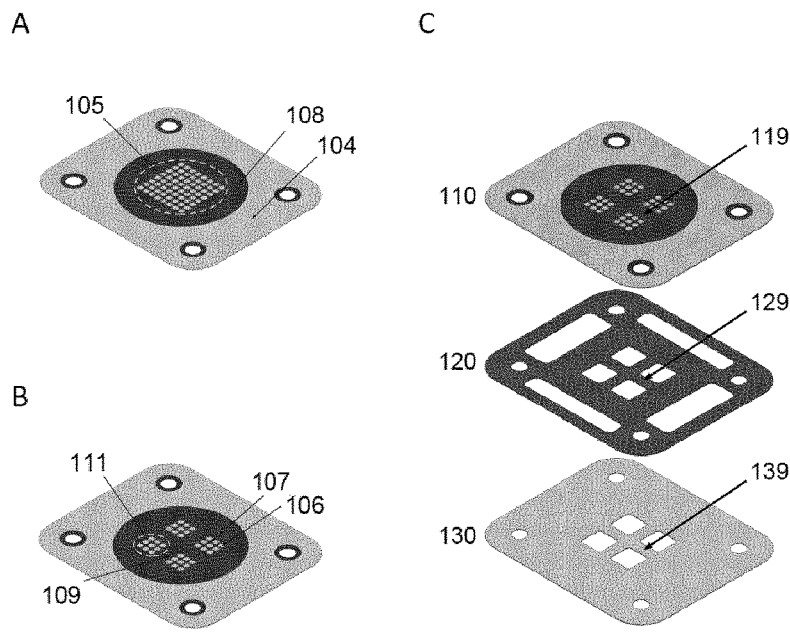
FIG. 3 shows an example of a capture layer (100). A) The capture layer (100) comprises an analyte capture zone (105) and a fastener zone (104). The analyte capture zone (105) is separated from the fastener zone (104) by a barrier zone (108). B) The analyte capture zone comprises capture divisions (106) which are delimited by a first divider (107). The capture divisions can be present as groups (111) which are delimited by a second divider (109). C) Exploded view of the capture layer, showing the extension of the second divider through all three layers: 119, second divider of the reactive layer, 129, second divider of the reinforcement layer, 139, second divider of the adherence layer.

Step 1: Patch consisting of capture layer (100) with removable cover (401) and sampling cover layer (200 P1) is provided.

Step 2: After removing removable cover (401), patch is attached to surface to be sampled. Buffer or reagent is applied to top hole (206) of sampling cover layer (200 P1).

Step 3: Patch is incubated. Optionally, sampling cover layer (200 P1) has no hole and forms complete occlusion, and incubation is performed with water transpired from surface (such as skin) and captured in said occlusion.

Step 4: Rigid support (300) is mounted to analysis stage and aligned with pins (403). Patch consisting of capture layer (100) and sampling cover layer (200 P1) is removed from surface to be sampled and mounted to rigid support (300) aligned with pins (403). At this point, optionally, additional wash buffer may be applied, and, if needed, incubated and removed by vacuum at the proximal surface (301) or the distal surface (202) of the stack.

Step 5: Sampling cover layer (200 P1) is removed, while capture layer (100) is kept in place with vacuum applied to rigid support (300), and adhesive at proximal surface (101) of capture layer (100).

Step 6: Capture layer (100) on rigid support (300), ready for analysis

Step 7: Analysis cover layer (200 P2)—after removing removable cover from proximal surface—is mounted to rigid support on analysis stage, aligned with pins (403), and attached with adhesive present at proximal surface (201). Analysis cover layer (200 P2) may be a conjugate pad that contains a reagent either in dry, gel, or aqueous form. Reagent is released 'as is', or by applying additional buffer, and incubated. At this point, optionally, additional wash buffer may be applied on the distal side, and processed as explained in Step 4. Absorber pad (402) collects reagent and/or buffer on the proximal side.

Step 8: Analysis cover layer (200 P2) is removed, while capture layer (100) is kept in place with vacuum applied to rigid support (300), and adhesive at proximal surface (101) of capture layer (100). At this point, optionally, steps 7 and 8 are repeated with different analysis cover layers (200 P3-P7) comprising different reagents, or the capture layer (100) is dried.

Step 9: Optical or electrical signal is measured on capture layer (100).

Figure 9:
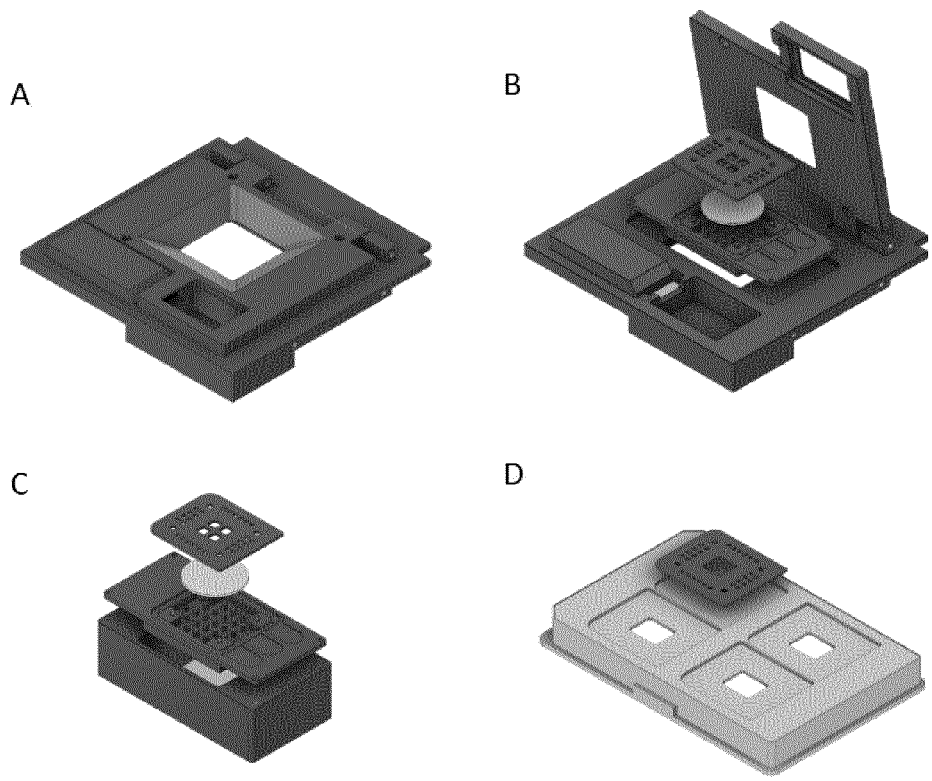

FIG. 9 shows different incubator/reader stages to be used with the patch according to invention. A, B) integrated stage for combined vacuum incubation and optical read out. C, D) separate vacuum incubator and adapter for standard microarray reader.

Figure 10:
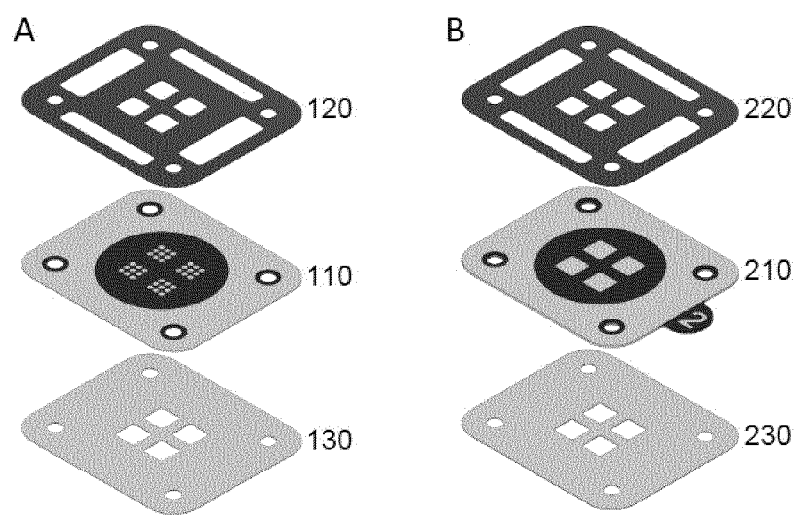

FIG. 10 shows an exploded view of a capture layer (A) and a cover layer (B) with an alternative order of reinforcement layer (120, 220), reactive layer (110, 210) and adherence layer (130, 230).

Figure 11:
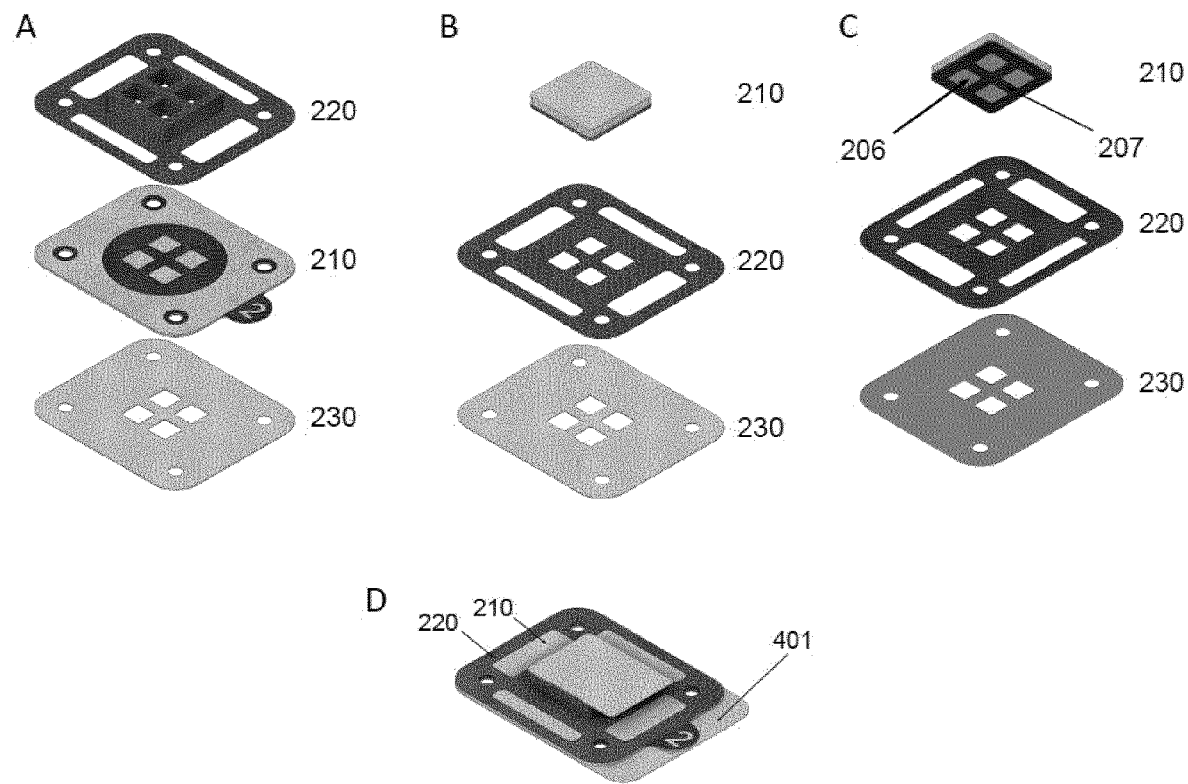

FIG. 11 shows three special variants of the cover layer (200). Due to their large thickness they are in particular suited for the analysis step that takes place when the capture layer (100) is mounted on the rigid support (300): A) has a thick reinforcement layer (220)—typically around 3 mm in thickness—that has pockets, which simplify dispensing buffer or liquid reagents. B) has a thick reactive layer (210)—typically around 2 mm in thickness—with reagent dividers (207) implemented only from the proximal side to a depth between 0.2-0.8 mm. If reagents are deposited in the reagent divisions (206) close to the proximal side, this variant of the cover layer (200) has the ability to spread buffer that is applied to the distal side of the reactive layer (210) evenly to the reagent divisions (206), whereby the buffer will concurrently reconstitute the stored reagents. If vacuum is applied to a stack composed of rigid support (300), capture layer (100), and cover layer (200) through the central openings (305), the reagents can be used for reactions in the capture layer (100), and backflow/mixture of the different reagents at the distal side of the reactive layer (210) can be avoided. C) shows the variant of B) looking from the proximal side. D) shows a cover layer (200)—identical to the one shown in A), however, with removable covers (liners) on distal and proximal surface, which can be used to hold a liquid reagent. Such liners can be used for all cover layers (200), presented in this document.

Figure 12:
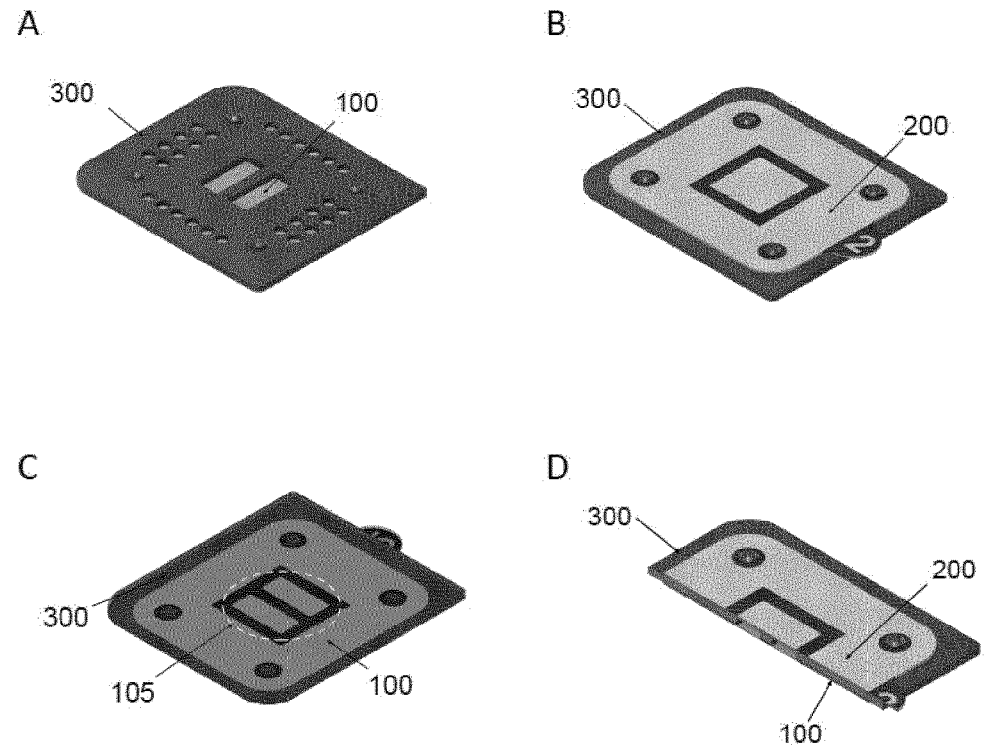

FIG. 12 illustrates a protocol alternative in which the rigid support (300) and the capture layer (100) are flipped over on the analysis stage to detect analytes bound to the proximal surface of the analyte capture zone (105). A) The proximal surface of the capture layer (100) can be seen through the central openings (305) of the rigid support (300). B) Analysis cover layer (200 P2) is attached to the other side of the rigid support (300). Capture layer (100) and analysis cover layer (200 P2) are separated by the rigid support (300). C) Same assembly as in B), shown from below. D) Cross section through the assembly shown in B).

Figure 13:
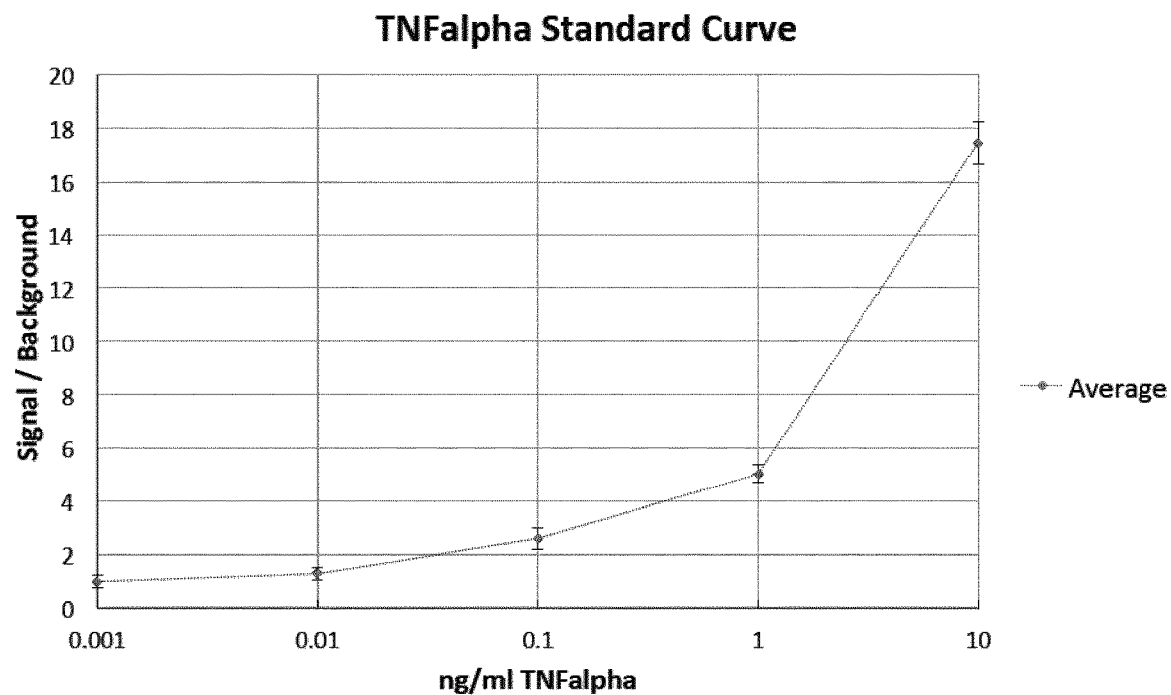

FIG. 13 shows TNFalpha standard curve. Average values and standard deviations of 3 replicates are shown for concentrations 1 pg/ml, 10 pg/ml, 100 pg/ml, 1 ng/ml, and 10 ng/ml (line connects the average data points).

REFERENCE NUMBERS

100 capture layer
101 proximal surface
102 distal surface
103 registration holes
104 fastener zone
105 analyte capture zone
106 capture division
107 first divider
108 barrier zone
109 second divider
110 reactive layer
111 group of capture divisions
119 second divider (in reactive layer)
120 reinforcement layer
129 second divider (in reinforcement layer)
130 adherence layer 133 adhesive (low tack)
135 adhesive (high tack)
139 second divider (in adherence layer)
200 cover layer
200 P1—sampling cover layer
200 P2, P3 . . . Pn—analysis cover layer
201 proximal surface
202 distal surface
203 registration holes
204 fastener zone
205 reagent zone
206 reagent division
207 reagent divider
208 barrier zone
209 tab for removal of cover layer
210 reactive layer
217 reagent divider (in reactive layer)
220 reinforcement layer
227 reagent divider (in reinforcement layer)
230 adherence layer
233 adhesive (low tack)
235 adhesive (high tack)
237 reagent divider (in adherence layer)
300 rigid support
301 proximal surface
302 distal surface
303 registration holes
304 fastener zone
305 central opening
306 vacuum openings
307 support divider
401 removable cover
402 absorber pad
403 pins
501 adapter

EXAMPLES

1. Patch Manufacturing Process

Handle material with gloves and keep material, in particular first and second water permeable material—at room temperature and <20% relative humidity unless stated otherwise. Finalise assembly of absorbent material into patches within one day, vacuum pack final product in Al/polymer composite pouch and store in fridge at 4° C.

Step 0: Obtain stock material. E.g.
  For (110): GE Lifescience nitrocellulose membrane (pore size 0.45 μm) in reel format (width 30 mm).
  For (210): GE Lifescience Fusion 5 glass fiber conjugate material in reel format (width 30 mm).
  For optional reinforcement layers (120) and (220): Similar to Folex polyester film with pressure sensitive adhesive for cold lamination, in reel format (width 30 mm).
  For layers (130) and (230): Avery Dennison Vancive MED 3044 film with pressure sensitive adhesive on both sides and liner on low tack skin side (width 30 mm).

Preparing Water Permeable Material (reactive layers (110) and (210))

Step 1: For (110) and (210) direct print first divider (107)/second divider (109)/barrier zone (108) pattern, and reagent divider (207)/barrier zone (208) pattern, respectively, using e.g. Markem Imaje food grade print head (400×450 dpi) using black wax based inks, with additional heat cure at typically 100° C. (depending on thermal properties of wax based ink used) in heated roller in custom 1-reel to 1-reel equipment. Thick material may require printing from both sides, and/or multiple overprints in order to achieve wax distribution throughout permeable materials.

(Alternatively, direct printing of UV curable ink using inkjet print head (e.g. Epson) or pad printing (e.g. Teca-Print), using UV curable black ink, with additional UV cure step in custom reel to reel equipment may be used. Please note that timing of additional UV cure after printing in 1-reel to 1-reel arrangement is critical to distributing ink throughout permeable materials and maintaining print pattern at the same time (and dependent on the UV curable ink used). Thick material may require printing from both sides, and/or multiple overprints in order to achieve this).

Step 2: Using e.g. Biodot RR120 standard 1-reel to 1-reel Web Handling Platform spot reagents onto nitrocellulose or glass fibre, incubate, block, wash, and dry. Nitrocellulose or glass fibre is handled directly on reels. Depending on requirements reagents may be spotted on top, bottom or both sides of nitrocellulose or glass fibre.

Preparing TPU Films and Mounting Reactive Layers Onto TPU Films

Step 3: In a standard medical patch 2-reel to 1-reel converting process, the TPU film is fed from the first source reel, printed nitrocellulose or printed glass fiber is fed from the second source reel, and the product of this step—either the capture layer (100) or the cover layer (200), on a liner—is fed to the destination reel. The following features are die cut into the TPU film from high tack side: (i) the 30 mm×40 mm outline of patch, (ii) desired openings in analyte capture (105) and reagent zones (205), respectively, taking into account second dividers (109) and reagent dividers (207), respectively, and (iii) registration holes (103) and (203), respectively. These features are cut into the TPU film down to, and including the low tack adhesive at the bottom of the TPU film. I.e. only leaving the TPU liner intact.

Figure 4:
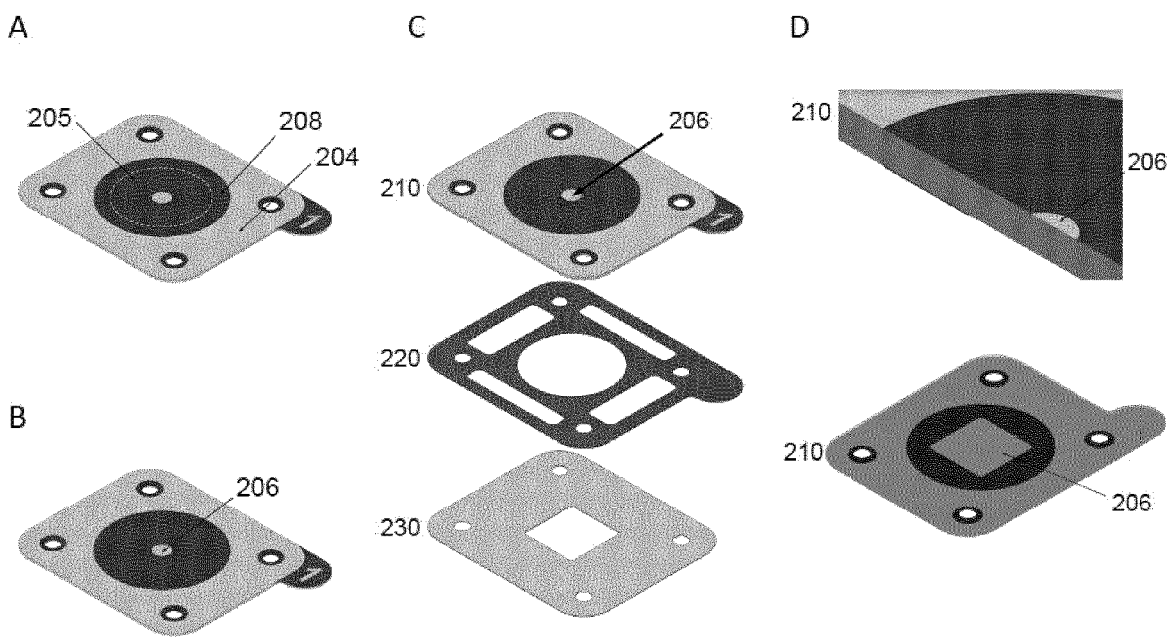
FIG. 4 shows an example of a cover layer for use during analyte collection (sampling cover layer, 200 P1). A) The cover layer comprises a reagent zone (205) and a fastener zone (204), which is separated from the reagent zone (205) by a barrier zone (208). B) The reagent zone comprises one reagent division (206). C) Exploded view of the sampling cover layer. D) The reagent division (206) in the reactive layer (210) of the sampling cover layer is shown from above (distal, magnified view, and scaled by factor 5 in distal direction with hidden lines shown) and below (proximal). It is advantageous if the reagent division has a small diameter on the distal side (to prevent evaporation of buffer). On the proximal side, the reagent division (206) of the sampling cover layer (200 P1) has the same dimensions as the analyte capture zone (105) of the capture layer (100). In the special case shown here this transition takes place within the reactive layer (210). The advantage of this embodiment is that buffer applied to the reagent divison (206) on the distal side is spread—by capillary force—to the same dimensions as the analyte capture zone (105) of the capture layer (100).
Figure 5:
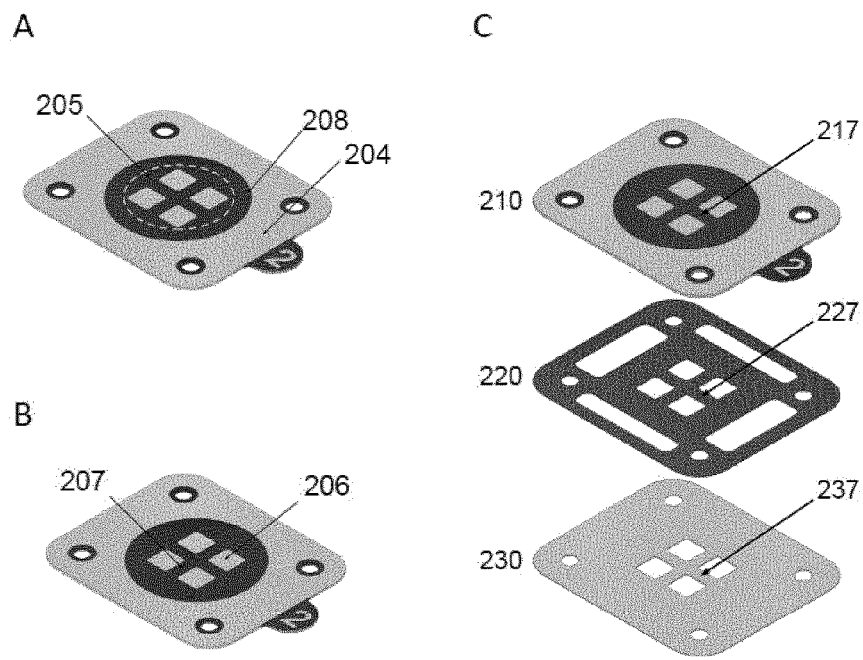
FIG. 5 shows an example of a cover layer for use during the analysis steps (analysis cover layer, 200 P2-P7). A) The cover layer comprises a reagent zone (205) and a fastener zone (204), which is separated from the reagent zone (205) by a barrier zone (208). B) The reagent zone (205) comprises several reagent divisions (206), which are delimited by a reagent divider (207). C) Exploded view of the analysis cover layer, showing the extension of the reagent divider through all three layers: 217, second divider of the reactive layer, 227, second divider of the reinforcement layer, 237, second divider of the adherence layer.
Figure 6:
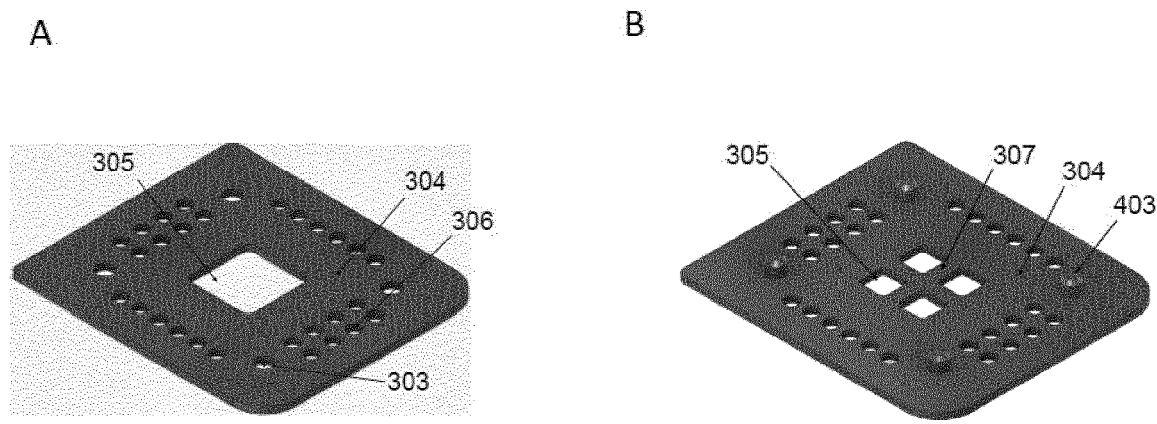
FIG. 6 shows examples of a rigid support (300). The rigid support comprises a fastener zone (304), and one or several central openings (305). If several central openings are present, they are delimited by a support divider (307). The rigid support further comprises vacuum openings (306) and registration holes (303) or alignment pins (403).

Except for (iii) the registration holes (103) and (203), respectively, which are cut all the way through the TPU film. At the same time those portions of the TPU film that contain the desired openings in analyte capture (105) and reagent zones (205), respectively (together with both adhesive layers) are removed, only leaving the TPU liner behind in these zones. The printed nitrocellulose or printed glass fiber, respectively, from the second reel is die cut into individual 30 mm×40 mm patches including registration holes (103) and (203), respectively. This die cutting step is optically aligned to the print pattern. Immediately after this, in a second step the latter patches are placed and laminated onto the exposed high tack side of the TPU film, using alignment by pins (403) and registration holes (103) and (203). In a final step, using e.g. an inkjet printer (i) company label, (ii) barcode with serial number, (iii) tab labels "1" and "2" as shown in FIGS. 4 and 5, and (iv) orientation mark are printed onto the distal side of the patch.

Step 3' (with optional reinforcement layers (120) and (220)): In a standard medical patch 3-reel to 1-reel converting process, TPU is fed from the first source reel, the polyester film is fed from the second source reel, printed nitrocellulose or printed glass fiber is fed from the third source reel, and the product of this step—either the capture layer (100) or the cover layer (200), on a liner—is fed to the destination reel. In addition to steps carried out in Step 3, in Step 3', depending on if the order of the layers is either (130), (120), (110), or (130), (110), (120), for the capture layer (100), and equally, either (230), (220), (210), or (230), (210), (220), for the cover layer (200), respectively, the following features are die cut into the polyester film from the second reel, either from the adhesive side or the non-adhesive side: (i) the 30 mm×40 mm outline of patch, (ii) desired openings in analyte capture (105) and reagent zones (205), respectively, taking into account second dividers (109) and reagent dividers (207), respectively, and (iii) registration holes (103) and (203), respectively. These features are cut all the way through the polyester film. In case the layer order is (130), (120), (110) or (230), (220), (210), respectively, immediately after this, in a second step, the resulting 30 mm×40 mm patches are placed and laminated onto the exposed high tack side of the TPU film, with the adhesive side of the polyester facing the distal side of the stack, using alignment by pins (403) and registration holes (103) and (203). Immediately after this, in a third step the printed nitrocellulose or printed glass fiber cut into 30 mm×40 mm patches as described in Step 3, are placed and laminated onto the exposed high tack side of the polyester film (and in some cases partially exposed high tack side of the TPU), using alignment by pins (403) and registration holes (103) and (203). In case the layer order is (130), (110), (120) or (230), (210), (220), respectively, in the said second step, the printed nitrocellulose or printed glass fiber cut into 30 mm×40 mm patches as described in Step 3, are placed and laminated onto the exposed high tack side of the TPU film, using alignment by pins (403) and registration holes (103) and (203). In the said third step, the 30 mm×40 mm polyester patches are placed and laminated onto the printed nitrocellulose or printed glass fiber, with the adhesive side of the polyester facing towards the proximal side of the stack, using alignment by pins (403) and registration holes (103) and (203).

Assembling Capture Layer (100) and Cover Layer (200)

Step 4: In a standard medical patch 2-reel to 1-reel converting process, the tape carrying the capture layer (100) patches is fed from the first source reel, and the tape carrying the cover layer (200) patches is fed from the second source reel, and the product of this step—a stack composed of the capture layer (100) and the cover layer (200), carried on a liner—is fed to the destination reel. In this converting step patches of cover layers (200) are released from their respective liner tape and placed and laminated onto the capture layer (100) patches using alignment by pins (403) and registration holes (103) and (203).

Cover layers (200) from Step 3 and 3' respectively, and stacks composed of capture layer (100) and (200) are now ready to be vacuum packed, either as strips of e.g. 10 patches, or single patches, depending on desired quantities in pouches.

Remarks

Screen printing, photostructurable dry and liquid resist are further options for introducing structured hydrophobic/waterproof areas in absorbent material.
TPU film may be prepared by one of many available medical patch material suppliers with converting capability.
Further to the improvement of mechanical stability, reinforcement layers (120) and (220) may also serve as a means to economise on nitrocellulose and glass fiber material consumption as the latter may be chosen smaller than the patch size, if reinforcement layers are employed.
Moreover, as long as capture divisions (106) and reagent divisions (206) are large enough, they may also be formed by several isolated nitrocellulose and glass fiber pieces, held in place by the reinforcement layers (120) and (220), instead of formation of said divisions (106) and (206) by hydrophobic dividers (107) and (207) in a single piece of nitrocellulose and glass fiber, respectively. In this case, after assembly, the adhesive bond between, reinforcement layers (120) and (220), and adherence layers (130) and (230) takes on the role of the hydrophobic dividers (107) and (207).
Alternatively, preparation of water permeable materials (reactive layers (110) and (210)), optionally, including reinforcement layers (120) and (220) may also be carried out employing batch processing of sheet instead of tape material. In this case spotting equipment as e.g. Biodot AD 2030 Aspirate Dispense Platform is used for spotting of reagents onto nitrocellulose or glass fibre. Custom equipment suitable for batch processing is then used for incubation, blocking, washing, and drying.
Rigid support (300) may be manufactured by machining, waterjet or laser cutting of polymer sheets procured as raw material in the desired thickness. Alternatively, rigid support (300) may also be obtained by mold processes, such as injection and transfer molding.

2. Protocol for Quantitative or Semi-Quantitative Detection of Antigen A and B

Patch comprising capture layer (100) and sampling cover layer (200 P1) with 4 groups of capture divisions (111) each one having 9 capture divisions (106) is provided. The capture divisions (106) comprise two antibodies, the first binding to antigen A, the second binding to antigen B. The 9 capture divisions (106) per group of capture divisions (111) are configured as follows: each antibody, to antigen A and B, is present in 3 capture divisions (106), i.e. the measurement of each antigen is present in 3 replicates. The remaining 3 capture divisions (106) are blank and are used as negative controls.
In this example the removable cover (401) has 2 parts. Both parts of the removable cover (401) include a tab that allows easy removal. One part covers 3 of the 4 groups of capture divisions, the other part covers the remainder of the proximal surface (101). First, the latter part is removed from the proximal (bottom) side (101) of the capture layer (100), exposing one group of capture divisions (111).
The patch is attached to a person's skin.
Buffer is added to a subgroup of reagent divisions (206) of the sampling cover layer (200 P1). These reagent divisions are in fluid connection to the exposed capture divisions (106).
Incubation on skin for 15 minutes.
Patch is removed from the skin.
Second part of the removable cover (401) is removed, exposing the rest of the capture divisions (106).
Patch is attached to rigid support (300).
Vacuum is applied to the capture layer (100) via vacuum openings (306) and central openings (305) in the rigid support (300).
Sampling cover layer (200 P1) is removed from the capture layer (100) while capture layer stays attached to the rigid support (300).

Analysis cover layer (200 S1) is attached to the capture layer (100) with one reagent division (206) in fluid connection with the first group of capture divisions (111). This group is the first of to those 3 groups of capture divisions (111) that have not been exposed during analyte collection from the skin (and therefore comprise no analyte). The said reagent division (206) comprises first known amounts of antigen A and antigen B (standard 1).

Vacuum is turned off.

Buffer is applied to said reagent division (206) and incubated for 5 minutes.

Vacuum is turned on, and remaining buffer is drawn through capture divisions (106) onto absorber pad (402).

Analysis cover layer (200 S1) is removed from the capture layer (100) while capture layer stays attached to the rigid support (300).

Analysis cover layer (200 S2) is attached to the capture layer (100) with one reagent division (206) in fluid connection with the second group of capture divisions (111). This group is the second of to those 3 groups of capture divisions (111) that have not been exposed during analyte collection from the skin (and therefore comprise no analyte). The said reagent division (206) comprises second known amounts of antigen A and antigen B (standard 2).

Vacuum is turned off.

Buffer is applied to said reagent division (206) and incubated for 5 minutes.

Vacuum is turned on, and remaining buffer is drawn through capture divisions (106) onto absorber pad (402).

Analysis cover layer (200 S2) is removed from the capture layer (100) while capture layer stays attached to the rigid support (300).

Analysis cover layer (200 S3) is attached to the capture layer (100) with one reagent division (206) in fluid connection with the third, and last, group of capture divisions (111). This group is the third of to those 3 groups of capture divisions (111) that have not been exposed during analyte collection from the skin (and therefore comprise no analyte). The said reagent division (206) comprises third known amounts of antigen A and antigen B (standard 3).

Vacuum is turned off.

Buffer is applied to said reagent division (206) and incubated for 5 minutes.

Vacuum is turned on, and remaining buffer is drawn through capture divisions (106) onto absorber pad (402).

Analysis cover layer (200 S3) is removed from the capture layer (100) while capture layer stays attached to the rigid support (300).

Analysis cover layer (200 S4) is attached to the capture layer (100). Analysis cover layer has 4 reagent division (206), each one of them in fluid connection with one of the four groups of capture divisions (111). The said reagent division (206) comprises no antigen, because analysis cover layer (200 S4) is used for washing all capture divisions (106).

Vacuum is turned off.

Buffer is applied to all reagent divisions (206).

Vacuum is turned on, and buffer is drawn through capture divisions (106) onto absorber pad (402).

Analysis cover layer (200 S4) is removed from the capture layer (100) while capture layer stays attached to the rigid support (300).

Analysis cover layer (200 P2) is attached to the capture layer (100). The reagent divisions (206) comprise a fluorophore-labelled secondary antibody specifically binding to the antibodies to antigens A and B now comprised in the capture divisions (106).

Vacuum is turned off.

Buffer is applied to all reagent divisions (206) and incubated for 5 min.

Vacuum is turned on, and remaining buffer is drawn through capture divisions (106) onto absorber pad (402).

Vacuum is turned off.

As a final wash step buffer is applied to all reagent divisions (206) and incubated for 5 min.

Vacuum is turned on, and remaining buffer is drawn through capture divisions (106) onto absorber pad (402).

Analysis cover layer (200 P2) is removed from the capture layer (100) while capture layer stays attached to the rigid support (300).

Fluorescence of capture divisions (106) on capture layer (100) mounted on rigid support is measured.

Remarks

The reader device is also able to supply the vacuum to the rigid support (300) for (i) holding the latter to the analysis stage (FIG. 9 A, B, C), (ii) varying the force with which the capture layer (100) is held to the rigid support (300), and (iii) applying the necessary vacuum to perform the immunofiltration process.

The reader device may have a smart device (such as an Apple iPhone, iPad, or Android device) interface to exchange data and control commands. Moreover, the user interface on the smart device may be employed for the interaction between the user and the reader device. Therefore, this interaction may also be voice controlled from the moment the user puts on gloves to the moment he puts them off. The idea being that the smart device is never touched with patient material in order to avoid contamination of the non-disposable parts of the test set-up, and to avoid cross-contamination between different tests.

Standards 1, 2, and 3 may also be applied concurrently using one analysis cover layer (200 S), if mixture of reconstituted standards can be avoided, by design of analysis cover layer (200 S) and/or by choosing sufficiently short incubation time.

Analysis cover layers (200 S4) and (200 P2) may also contain preloaded reagents and buffers in liquid form.

Wash cover layer (200 S4) may also consist of a hydrophobic frame only—similar to rigid support (300)—that serves to guide applied buffer into the respective groups of capture divisions.

Quantitative results may also be obtained by carrying out periodic measurement of a calibration curve using a dedicated patch that is not used to collect sample from skin assuming that intra-batch variations are sufficiently small. E.g. if a package of tests contains 10 patches, 1 patch is used to generate a calibration curve that can be used to quantify the results on the other 9 patches. The data of the calibration curve is stored on the reader device in order to be able to retrieve it when the other 9 patches are used, whereby the identification printed on the patches may be used to correctly associate calibration data in case several test packages are used concurrently on the reader device.

In many cases semi-quantitative results will only be required. In this case, only one standard may be used to define the threshold between a negative and positive result of the test.

In analogy to above protocol, not only 2 antigens A and B, but also 1 or more than 2 antigens may be detected.

More than one capture layer (100) may be stacked on top of each other. If the capture divisions on different layers capture different analytes, multiplex in vertical direction is possible in addition to the multiplex described in this protocol.

3. Measurement of TNFalpha Standard Curve

FIG. 13 shows the standard curve of an assay where the antigen is TNFalpha as an example. The curve shown here was obtained during development of the patch by dispensing a dilution series of a TNFalpha standard directly onto the capture divisions (106) and measuring the fluorescence. Three replicates have been used to calculate average and standard deviation for each datapoint. For the blank capture division (106)—the background—standard deviation of 0.3 is obtained on the signal/background scale. Therefore, a limit of detection (at 3 times the standard deviation) of approximately 100 pg/ml can be determined from the curve shown in FIG. 13.

4. Specific Advantages of the Invention

The patch is a multipart (at least 2 parts) stacked structure. Each part is composed of a membrane, with either water permeable (=channels) or water impermeable zones, and a frame-shaped liquid proof layer that has high tack permanent adhesive on the side facing the membrane and a re-usable low tack adhesive on the opposite side. Both adhesives are liquid proof.

The first part is called a capture layer (100) and contains a reactive layer (110) with capture divisions (106). Capture ligands can be implemented on either or both sides of the reactive layer (110) contained in capture layer (100). E.g. for IgG antibodies on nitrocellulose capture ligands are confined to within 3-6 micrometers perpendicular to the reactive layer (110), if the IgG is applied by contactless ink jetting. In this example the remainder of the capture division (106) in the reactive layer (110) would be blocked by e.g. BSA.

Larger analytes, such as microorganisms or fragments thereof are typically captured on the proximal surface of the reactive layer (110), whereas smaller analytes, such as proteins, molecules, and ions can be captured on either or both surfaces of the reactive layer (110).

The second part is called a cover layer (200) and contains a reactive layer (210) with reagent divisions (206). This part is called (200 P1), in particular, after pad 1, i.e. the first pad to be applied to stack. The reagent is implemented inside the reactive layer (210) contained in (200 P1). E.g. a surfactant with the capability of boosting the extraction efficiency is applied to a bound glass fiber by contactless ink jetting.

Furthermore, for analysis the patch is mounted on a rigid support (300), which gives the stack stability for handling and applying liquids with/without hydrostatic pressure or back pressure of a gas volume, and/or extracting liquids with vacuum to either or both sides.

On the rigid support (300) capture (100) and cover layers (200) can be taken apart and re-assembled at least 5 times and still retain their structural and liquid proof properties.

The rigid support (300) has vacuum openings (306) to hold the capture layer (100) firmly in place (additionally to the adhesive force that the adhesive exerts) that allows peeling of cover layers (200) while the capture layer (100) stays in place, due to the higher total adhesion force (vacuum+adhesive) between rigid support (300) and capture layer (100) compared to capture layer (100) and cover layers (200).

Several cover layers (200) may be applied/removed consecutively, each one containing different reagents (200 P1, 200 P2, . . . 200 Pn. Reagents can be dried, lyophilized, in gel or liquid form. Unless they are already liquid, they will be reconstituted by a buffer solution that is applied to one or more ports in cover layer (200).

The stack of capture layer (100) and sampling cover layer (200 P1) is attached to skin for analyte collection, with capture layer (100) attached to skin with said re-usable adhesive, and sampling cover layer (200 P1) attached to capture layer (200) with said re-usable adhesive, and sampling cover layer (200 P1) containing an analyte extraction reagent.

The stack is attached to the rigid support (300) for analysis with capture layer (100) attached to rigid support (300) with said re-usable adhesive, and analysis cover layer (200 P2) attached to capture layer (100) with said re-usable adhesive. For this, sampling cover layer (200 P1) is removed and analysis cover layer (200 P2) is attached instead and processed (and so on if further reagents are needed depending on protocol).

Also more than one capture layer (100) can be employed e.g. to implement multiplex in direction perpendicular to the reactive layers (110).

Channels of water permeable material are the only connection between the proximal (101, 201) and distal surfaces (102, 202) of the capture layers (100) and cover layers (200), respectively, even if they are stacked together. Channels lead though capture divisions (106) and reagent divisions (206) only.

Other than through channels, for liquids, proximal (101, 201) and distal surfaces (102, 202) of capture layers (100), cover layers (200), and stacks thereof, respectively, are isolated from each other.

Channels are aligned to each other between capture layers (100) and cover layers (200) by use of registration holes (103, 203) (for manufacturing and application) that are present on both capture layers (100) and cover layers (200), and that are aligned by pins (403).

Channels on capture layers (100) may be assigned to channels on other capture layers (100) and cover layers (200) by one or more selected from the group of following relationships: a one to many, many to one, one to one, and many to many relationship. This assignment can also be varied during carrying out the assay by using differently structured cover layers (200).

In this way—by implementing more than one channel through a cover layer (200)—several laterally independent reagent compartments can be formed, each one connecting to another group of channels in the capture layer (100).

Figure 7:
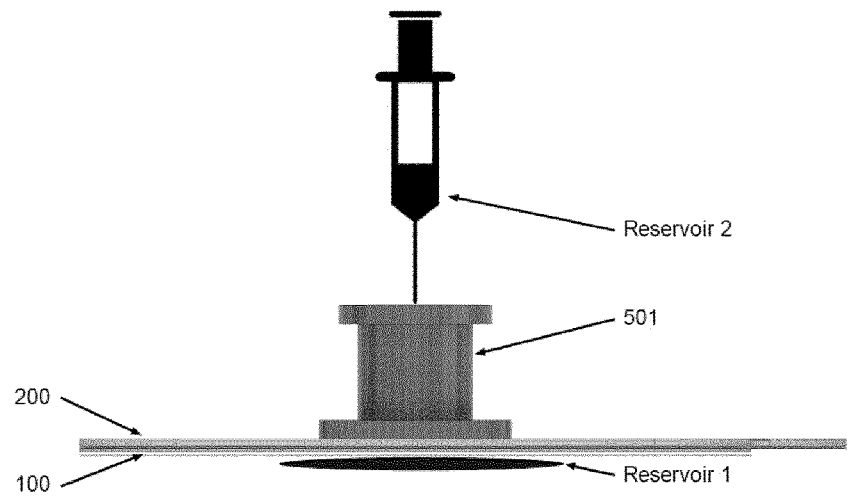
FIG. 7 shows a sketch of liquid communication between reservoir 1 and reservoir 2 through channels formed by capture layer (100) and cover layer (200). Reservoir 1 corresponds to the pocket between capture layer (100) and skin surface, bounded by acrylic adhesive attaching the capture layer (100) to the skin. Reservoir 1 corresponds to the volume in a liquid delivery device, e.g. a syringe.
Figure 8:
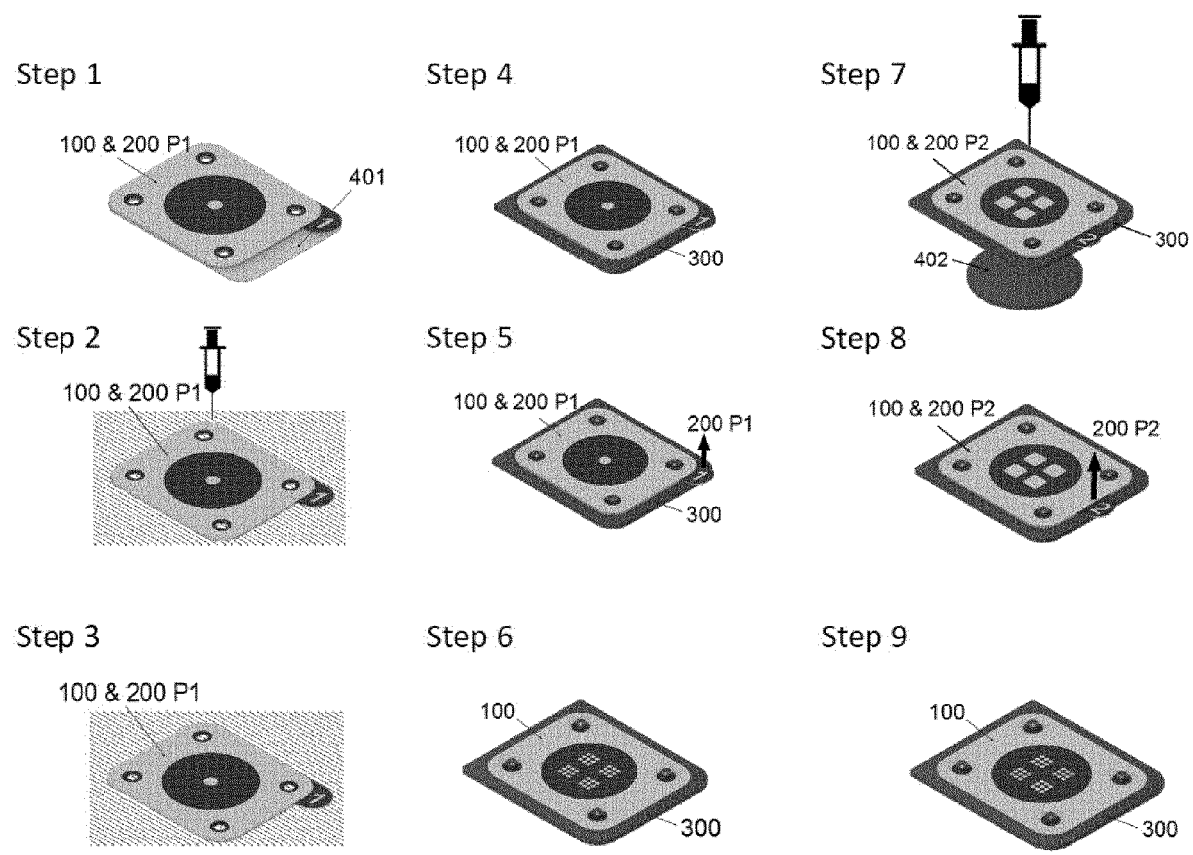
FIG. 8 illustrates a basic protocol for using the patch according to the invention.

2 liquid reservoirs communicate through the stack with each other (see FIG. 7):

During analyte collection: reservoir 1 (R1) is the pocket between skin and capture layer (100), and reservoir 2 (R2) is the extraction buffer reservoir, e.g. syringe, pipette, dropper or liquid delivery cartridge used with or attached to cover layer (200 P1). By transferring, said buffer from R2 to R1 it comes in contact with the skin surface. Then, the buffer is incubated and, optionally, if e.g. a syringe is used, pumped in reverse, to transfer the buffer from R1 back to R2. In this way, as many analytes as possible (now dissolved in said buffer) are moved past the capture ligands.

This is the well-known procedure of immunofiltration, which, e.g. in the case of antibodies as affinity molecules, may shorten the time for generation of the antigen-antibody complex from 30-60 minutes to only 5 minutes.

During analysis: R1 is the absorption pad (below rigid support (300)), and R2 is the reconstitution buffer reservoir, e.g. syringe pipette, dropper or liquid delivery cartridge used with or attached to cover layer (200). By releasing said buffer to the cover layer (200) the reagent is reconstituted during a short incubation step. If e.g. a syringe is used, it is pumped first to an intermediate point in the latter step, and after incubation pumped forward to the endpoint, to push said buffer with the reconstituted reagent through capture divisions (106), again as in the immunofiltration procedure. Similarly, if e.g. a dropper is used, to deliver the reconstitution buffer this 2 step process can be implemented by turning the vacuum at the proximal side of the rigid support (300) on and off after the reagent has been reconstituted and incubated by said buffer.

Optionally, cover layers (200) have an adaptor (501) with a suitable fitting for a tube in order to aid tight connection of R2 to a syringe, a pipette or a liquid delivery cartridge. This can also be a multiport fitting if cover layer (200) has several reagent divisions (206) that have to be isolated from each other. Instead of the centrifugal force that may also be applied, analytes, reagents, and buffers are moved here by the action of static pressure and vacuum. Alternatively they can also be moved by electrophoresis (as in Western Blotting).

Tabs for removal of cover layer (209) are present on cover layers (200) that enable easy removal. The analysis stage (FIG. 9 B, C) features corresponding grooves for said tabs (209) that prevents mis-oriented assembly of cover layers (200).

The flexible structure of the stack composed of capture layer (100) and cover layer (200) allows easy sampling on curved surfaces, such as e.g. skin, mucous membranes (e.g. in mouth and throat), but not limited to these.

Moreover, it also allows processing of other samples such as cell lysates, tissue extracts, serum, plasma, derivative of blood, full blood, saliva, or urine if used on the rigid support (300) already in the analyte collection step.

The rigid support (300) allows easy handling in analysis step (and, if required, storage) of processed capture layers (100).

The rigid support (300) and registration holes (103, 203, 303) allow for easy and accurate attachment and reading of processed capture layers (100) on standard optical reader equipment (e.g. confocal laser scanning microscope or microarray scanner).

Due to the filter action of the capture layer (100)—given by the pore size of the material used for the reactive layer (110)—large analytes—such as bacteria and fungi, or fragments, such as cell membrane fragments thereof—can be captured on the proximal surface (101) facing the skin surface, and smaller analytes—such as proteins, molecules and ions can be captured on the distal surface (102), or on both surfaces. In this mode suitable affinity molecules are implemented on both sides of the reactive layer (110) contained in the capture layer (100).

The rigid support (300) allows easy handling for the analysis on proximal (101) and distal surfaces (102) of the reactive layer (110) if the dual side mode is used shown in FIG. 12.

The adaptor (501) allows coupling of an ultrasonic transducer to the skin surface. In the context of the present specification, an ultrasonic transducer is a transducer that is able to convert electrical signal to ultrasound waves. The ultrasound waves enhance the extraction of analytes from the epidermis.

Another application of the invention is to perform concurrent antibody cross-reactivity tests in which at once the reaction of approximately 100 antibodies can be tested against an antigen.

Items

1. A flexible planar patch comprising
   a. a capture layer (100) having a proximal surface (101) and a distal surface (102), wherein said capture layer (100) is characterized by a thickness of 10 µm to 2 mm, particularly to 25 µm to 1 mm, more particularly 50 µm to 500 µm, even more particularly approximately 200 µm,
   and wherein said capture layer (100) comprises
      i. an analyte capture zone (105) extending from said proximal surface (101) to said distal surface (102), said analyte capture zone (105) consisting of a first water permeable material, said first water permeable material comprising a ligand capable of binding specifically to an analyte; and
      ii. a fastener zone (104) which is impermeable to water and/or delimited from said analyte capture zone by a water impermeable barrier zone (108), said fastener zone (104) comprising, on said proximal surface (101), an adhesive (133) capable of fastening said capture layer (100) removably to a surface; and
   b. a cover layer (200) having a proximal surface (201) and a distal surface (202), said cover layer comprising, on said proximal surface (201), an adhesive (233) capable of fastening said cover layer (200) removably to said capture layer (100).

2. The patch according to item 1, wherein said analyte capture zone (105) is compartmentalized into a plurality of confined water permeable capture divisions (106), particularly 1-1000, more particularly 1-256 capture divisions (106), wherein each of said capture divisions (106) comprises said ligand capable of binding specifically to an analyte and is separated by a first divider (107) that is impermeable to water.

3. The patch according to item 2, wherein said plurality of capture divisions (106) is divided into groups of capture divisions (111), particularly 1-50 groups of capture divisions (111), more particularly 1-16 groups of capture divisions (111), wherein each of said groups of capture divisions (111) is separated by a second divider (109) that is impermeable to water.

4. The patch according to any one of the preceding items, wherein said capture zone (105) is located in the centre of said capture layer (100) and said fastener zone (104) is located at the perimeter of said capture layer (100).

5. The patch according to any one of the above items, wherein the peel adhesion between said cover layer (200) and said capture layer (100) is between 0.1 N/25 mm and 5 N/25 mm.

6. The patch according to any one of the above items, wherein said cover layer (200) comprises
   a. a reagent zone (205) extending from said proximal surface (201) to said distal surface (202), said reagent zone (205) consisting of a second water permeable material, and
   b. a fastener zone (204) which is impermeable to water and/or delimited from said reagent zone (205) by a water impermeable barrier zone (208).

7. The patch according to item 6, wherein said reagent zone (205) is compartmentalized into a plurality of confined water permeable reagent divisions, particularly 1-144, more particularly 1-64, more particularly 1-36, more particularly 1-16 reagent divisions (206), wherein each of said reagent divisions (206) is separated by a reagent divider (207) that is impermeable to water. 8. The patch according to any one of items 6 or 7, wherein said reagent zone (205) comprises an adaptor (501) designed to connect said reagent zone to a confined volume and/or to an ultrasonic transducer.

9. The patch according to any one of items 6 to 8, wherein said reagent divisions (206) comprise a reagent, in particular a reagent selected from the group comprising an acid, a base, a salt, a sugar, a surfactant, a protein, a nucleic acid, an antimicrobial agent, in particular an antibacterial and/or an antifungal agent, a dye, a fluorophore, a lanthanide, an upconverting phosphor nanoparticle, colloidal gold, a cellulose nanobead, latex, a reagent for total protein quantification, an affinity molecule, in particular an antibody, an aptamer, an enzyme, a molecularly imprinted polymer, a ionophore, a pore or motor protein for nucleic acid sequencing, a nanoparticle, a microbead, more particularly a reagent selected from a reagent selected from an acid, a base, a salt, a sugar, a surfactant, a protein, a fluorophore, an upconverting phosphor nanoparticle, colloidal gold, a reagent for total protein quantification and an antibody, wherein in particular said reagent is in dried, lyophilized, gel or aqueous form, and wherein in particular said reagent is immobilised on a microbead or nanoparticle.

10. The patch according to any one of the above items, wherein said proximal surface (101) of said capture layer (100) is sealed with a removable cover (401).

11. The patch according to any one of the above items, wherein said capture layer (100) is attached to a rigid support (300) having a proximal surface (301) and a distal surface (302),
   a. wherein said rigid support (300) comprises
   b. a fastener zone (304) to which said proximal surface (101) of said capture layer (100) is attached,
   c. a central opening (305) which is aligned with said analyte capture zone (105) of said capture layer (100).

12. The patch according to item 11, wherein said rigid support (300) comprises vacuum openings (306) designed to apply a vacuum to said proximal surface (101) of said capture layer (100).

13. The patch according to any one of items 11 or 12, wherein said capture layer (100), said cover layer (200) and said rigid support (300) each comprise registration holes (103, 203, 303) for aligning them.

14. The patch according to any one of the above items, wherein said capture layer (100) and said cover layer (200) each comprise
   a. an adherence layer (130, 230) comprising said adhesive (133, 233)
   b. a reactive layer (110, 210) comprising said analyte capture zone (105) or said reagent zone (205) and
   c. optionally a reinforcement layer (120, 220).

15. The patch according to any one of the above items, wherein said first water permeable material is or comprises nitrocellulose.

16. The patch according to any one of items 6 to 15, wherein said second water permeable material is selected from the group comprising glass fibre, cotton, non-woven polyester and cellulose.

17. The patch according to any one of the above items, wherein said first divider (107), said second divider (109) and/or said reagent divider (207) comprise a layer of hydrophobic material introduced in said reactive layer (110, 210), wherein in particular said hydrophobic material extends from said proximal surface (101, 201) to said distal surface (102, 202) of said reactive layer (110, 210).

18. The patch according to any one of the above items, wherein said second divider (109) and/or said reagent divider (207) are formed by
   a. a layer of hydrophobic material introduced in said reactive layer (110, 210), wherein in particular said hydrophobic material extends from said proximal surface (101, 201) to said distal surface (102, 202) of said reactive layer (110, 210), and
   b. the adherence layer (130, 230), and
   c. optionally reinforcement layer (120, 220).

19. The patch according to any one of the above items, wherein at the interface of said proximal surface (101) of said capture layer (100) and said distal surface (202) of said cover layer (200) a capture division (106) and a reagent division (206) are in fluid connection and sealed from the surrounding area by a water impermeable barrier comprising said first divider (107) and/or said second divider (109) and said reagent divider (207).

20. The patch according to any one of items 1 to 5, 10 to 15, 17 or 18, wherein said planar cover layer is impermeable to water.

21. The patch according to any one of the above items, wherein the patch is configured as
   a. a patch for multiplex detection of analytes;
   b. a patch for detection of analytes on human or animal skin;
   c. a patch for detection of analytes by an immunological method and/or
   d. a diagnostic patch.

22. A patch assembly kit, comprising
   a. a capture layer (100) having a proximal surface (101) and a distal surface (102),
      said capture layer comprising
      i. an analyte capture zone (105) extending from said proximal surface (101) to said distal surface (102), said analyte capture zone (105) consisting of a first water permeable material, said first material comprising a ligand capable of binding specifically to an analyte; and
      ii. a fastener zone (104) which is impermeable to water and/or delimited from said analyte capture zone by a water impermeable barrier zone (108), said fastener zone (104) comprising, on said proximal surface (101), an adhesive (133) capable of fastening said capture layer (100) removably to a surface, and
   b. a sampling cover layer (200 P1) having a proximal surface (201) and a distal surface (202),
      said sampling cover layer comprising a fastener zone (204), said fastener zone (204) comprising, on said proximal surface (201), an adhesive (233) capable of fastening said sampling cover layer (200) removably to said capture layer (100); and c. an analysis cover layer (200 Pn) having a proximal surface (201) and a distal surface (202),
said analysis cover layer (200 Pn) comprising
   i. a reagent zone (205) extending from said proximal surface (201) to said distal surface (202), said reagent zone (205) consisting of a second water permeable material; and
   ii. a fastener zone (204) impermeable to water and/or delimited from reagent zone by a water impermeable barrier zone (208), said fastener zone (204) comprising, on said proximal surface (201), an adhesive (233) capable of fastening said sampling cover layer (200) removably to said capture layer (100); and
d. a rigid support (300) having a proximal surface (301) and a distal surface (302), wherein said rigid support (300) comprises a fastener zone (304) and a central opening (305).

23. The patch assembly kit according to item 21, wherein said rigid support (300) comprises vacuum openings (306) designed to apply a vacuum to said proximal surface (101) of said capture layer (100).

24. The patch assembly kit according to any one of items 21 or 23, wherein said sampling cover layer (200 P1) comprises
a. a reagent zone (205 P1) extending from said proximal surface (201 P1) to said distal surface (202 P1), said reagent zone (205 P1) consisting of said second water permeable material, and
b. a fastener zone (204 P1) which is impermeable to water and/or delimited from said reagent zone (205 P1) by a water impermeable barrier zone (208 P1).

25. The patch assembly kit according to any one of items 21 to 24, wherein said analyte capture zone (105) is compartmentalized into a plurality of confined water permeable capture divisions (106), particularly 1-1000, more particularly 1-256, wherein each of said capture divisions (106) comprises said ligand capable of specifically binding to said analyte, and is separated by a first divider (107) that is impermeable to water.

26. The patch assembly kit according to any one of items 21 to 25, wherein said reagent zone (205) is compartmentalized into a plurality of confined water permeable reagent divisions (206), particularly 1-144, more particularly 1-64, more particularly 1-36, even more particularly 1-16 reagent divisions (206), wherein each of said reagent divisions (206) is separated by a reagent divider (207) that is impermeable to water.

27. The patch assembly kit according to any one of items 21 to 26, wherein said reagent divisions (206) comprise a reagent, in particular a reagent selected from the group comprising an acid, a base, a salt, a sugar, a surfactant, a protein, a nucleic acid, an antimicrobial agent, in particular an antibacterial and/or an antifungal agent, a dye, a fluorophore, lanthanides, upconverting phosphor nanoparticles, colloidal gold, a cellulose nanobead, latex, a reagent for total protein quantification, an affinity molecule, in particular an antibody, an aptamer, an enzyme, a molecularly imprinted polymer, a ionophore, a pore or motor protein for nucleic acid sequencing, a nanoparticle, a microbead, more particularly said reagent is selected from an acid, a base, a salt, a sugar, a surfactant, a protein, a fluorophore, an upconverting phosphor nanoparticle, colloidal gold, a reagent for total protein quantification and an antibody, wherein in particular said reagent is in dried, lyophilized, gel or aqueous form, and wherein in particular said reagent is immobilised on a microbead or nanoparticle.

28. The patch assembly kit according to any one of items 21, 23 or 25 to 27, wherein said sampling cover layer (200 P1) is impermeable to water.

29. A diagnostic method comprising
a. providing a planar patch comprising
   i. a capture layer (100) having a proximal surface (101) and a distal surface (102),
   said capture layer comprising
      1. an analyte capture zone (105) extending from said proximal surface (101) to said distal surface (102), said analyte capture zone (105) consisting of a first water permeable material, said first water permeable material comprising a ligand capable of binding specifically to an analyte; and
      2. a fastener zone (104) which is impermeable to water and/or delimited from said analyte capture zone by a water impermeable barrier zone (108), said fastener zone (104) comprising, on said proximal surface (101), an adhesive (133) capable of fastening said patch removably to a surface, and
   ii. a sampling cover layer (200 P1) having a proximal surface (201) and a distal surface (202),
   said sampling cover layer comprising, on said proximal surface (201), an adhesive (233) capable of fastening said sampling cover layer (200) removably to said capture layer (100); wherein said analyte capture zone (105) comprises an analyte bound to said ligand;
b. providing a rigid support (300) having a proximal surface (301) and a distal surface (302), wherein said rigid support (300) comprises
   i. a fastener zone (304),
   ii. a central opening (305) and
   iii. vacuum openings (306);
   and attaching said planar patch to said distal surface (302) of said rigid support (300);
c. optionally applying an aqueous solution to said reagent zone (205) and applying a first vacuum to said proximal surface (101) of said capture layer (100), wherein said aqueous solution is directed
   i. from said reagent zone (205)
   ii. via said analyte capture zone (105)
   iii. to a liquid reservoir/absorber pad (402) below said central opening (305);
d. removing said sampling cover layer (200 P1) from said capture layer (100) under application of a second vacuum to said proximal surface (101) of said capture layer (100);
e. attaching to said capture layer (100) an analysis cover layer (200 P2) having a proximal surface (201) and a distal surface (202), said analysis cover layer (200 P2) comprising
   i. a reagent zone (205) extending from said proximal surface (201) to said distal surface (202), wherein said reagent zone (205) consists of a second water permeable material and comprises a reagent, in particular a reagent selected from the group comprising an acid, a base, a salt, a sugar, a surfactant, a protein, a nucleic acid, an antimicrobial agent, in particular an antibacterial and/or an antifungal agent, a dye, a fluorophore, lanthanides, upconverting phosphor nanoparticles, colloidal gold, cellulose nanobead, latex, a reagent for total protein quantification, an affinity molecule, in particular an antibody, an aptamer, an enzyme, a molecularly imprinted polymer, a ionophore, a pore or motor protein for nucleic acid sequencing, a nanoparticle, a microbead, more particularly said reagent is selected from an acid, a base, a salt, a sugar, a surfactant, a protein, a fluorophore, an upconverting phosphor nanoparticle, colloidal gold, a reagent for total protein quantification and an antibody, wherein in particular said reagent is in dried, lyophilized, gel or aqueous form, and wherein in particular said reagent is immobilised on a microbead or nanoparticle;
  ii. a fastener zone (204) impermeable to water and/or delimited from reagent zone by a water impermeable barrier zone (208), said fastener zone (204) comprising, on said proximal surface (201), an adhesive (233) capable of fastening said sampling cover layer (200) removably to said capture layer (100);
f. applying an aqueous solution to said reagent zone (205), and applying said first vacuum to said proximal surface (101) of said capture layer (100), wherein said aqueous solution is directed
  i. from said reagent zone (205)
  ii. via said analyte capture zone (105)
  iii. to a liquid reservoir/absorber pad (402) below said central opening (305);
g. removing said analysis cover layer (200 P2) from said capture layer (100) under application of said second vacuum to said proximal surface (101) of said capture layer (100);
h. optionally repeating steps e to g 1 to 5 times, particularly 1 to 2 times, using a different analysis cover layer (200 Pn);
i. detecting said analyte comprised in said analyte capture zone (105), particularly by a detection method selected from electrical detection, magnetic field detection, thermal detection and optical detection, more particularly by a detection method selected from impedance spectroscopy, voltammetry, Ion Selective Field Effect Transistors (ISFET)-based detection, magnetic field sensor, thermal contrast measurement, colour change, luminescence (including fluorescence and chemiluminescence) or turbidity measurement.

30. A diagnostic method comprising
a. providing a planar patch comprising a capture layer (100) as specified in any one of items 1 to 5, 10, 11, 13 to 15 or 17 to 19, and a sampling cover layer (200 P1) as specified in any one of items 1, 5 to 9, 13, 14 or 16 to 20; wherein the analyte capture zone (105) comprised in the capture layer (100) comprises an analyte;
b. providing a rigid support (300) as specified in items 11 to 13, and attaching said planar patch to the distal surface (302) of said rigid support (300);
c. optionally applying an aqueous solution to said reagent zone (205) and applying a first vacuum to said proximal surface (101) of said capture layer (100), wherein said aqueous solution is directed
  i. from said reagent zone (205)
  ii. via said analyte capture zone (105)
  iii. to a liquid reservoir/absorber pad (402) below said central opening (305);
d. removing said sampling cover layer (200 P1) from said capture layer (100) under application of said second vacuum to said proximal surface (101) of said capture layer (100);
e. attaching to the capture layer (100) an analysis cover layer (200 P2) as specified in any one of items 1, 5 to 9, 13, 14 or 16 to 19;
f. applying an aqueous solution to said reagent zone (205), and applying said first vacuum to said proximal surface (101) of said capture layer (100), wherein said aqueous solution is directed
  i. from the reagent zone (205)
  ii. via the analyte capture zone (105)
  iii. to a liquid reservoir/absorber pad (402) below the central opening (305) of the rigid support (300);
g. removing said analysis cover layer (200 P2) from said capture layer (100) under application of said second vacuum to said proximal surface (101) of said capture layer (100);
h. optionally repeating steps e to g 1 to 5 times, particularly 1 to 2 times using a different analysis cover layer (200 Pn);
i. detecting said analyte comprised in said analyte capture zone (105), particularly by a detection method selected from electrical detection, magnetic field detection, thermal detection and optical detection, more particularly by a detection method selected from impedance spectroscopy, voltammetry, Ion Selective Field Effect Transistors (ISFET)-based detection, magnetic field sensor, thermal contrast measurement, colour change, luminescence (including fluorescence and chemiluminescence) or turbidity measurement.

31. The diagnostic method according to any one of items 29 to 30, wherein
a. said analyte capture zone (105) is compartmentalized into a plurality of confined water permeable capture divisions (106); and
b. said reagent zone (205) is compartmentalized into a plurality of confined water permeable reagent divisions (206),
and wherein at the interface of said proximal surface (101) of said capture layer (100) and said distal surface (202) of said cover layer (200) a capture division (106) and a reagent division (206) are in fluid connection and sealed from the surrounding area by a water impermeable barrier.

32. A diagnostic method comprising
a. providing a planar patch comprising
  i. a capture layer (100) having a proximal surface (101) and a distal surface (102), said capture layer comprising
    1. an analyte capture zone (105) extending from said proximal surface (101) to said distal surface (102), said analyte capture zone (105) consisting of a first water permeable material, said first water permeable material comprising a ligand capable of binding specifically to an analyte; and
    2. a fastener zone (104) which is impermeable to water and/or delimited from said analyte capture zone by a water impermeable barrier zone (108), said fastener zone (104) comprising, on said proximal surface (101), an adhesive (133) capable of fastening said patch removably to a surface, and
  ii. a sampling cover layer (200 P1) having a proximal surface (201) and a distal surface (202),
    said sampling cover layer comprising, on said proximal surface (201), an adhesive (233) capable of fastening said sampling cover layer (200) removably to said capture layer (100);
  wherein said analyte capture zone (105) comprises an analyte bound to said ligand;
b. providing a rigid support (300) having a proximal surface (301) and a distal surface (302), wherein said rigid support (300) comprises i. a fastener zone (304),
ii. a central opening (305) and
iii. vacuum openings (306);
and attaching said planar patch to said proximal surface (301) of said rigid support (300);
c. optionally applying an aqueous solution to said reagent zone (205) and applying a first vacuum to said proximal surface (101) of said capture layer (100), wherein said aqueous solution is directed
i. from said reagent zone (205)
ii. via said analyte capture zone (105)
iii. to a liquid reservoir/absorber pad (402) below said central opening (305);
d. removing said sampling cover layer (200 P1) from said capture layer (100) under application of a second vacuum to said proximal surface (101) of said capture layer (100);
e. inverting said rigid support (300), resulting in a downwards oriented distal surface (102) of the capture layer (100);
f. attaching to said distal surface (302) of said rigid support (300) an analysis cover layer (200 P2) having a proximal surface (201) and a distal surface (202), said analysis cover layer (200 P2) comprising
i. a reagent zone (205) extending from said proximal surface (201) to said distal surface (202), wherein said reagent zone (205) consists of a second water permeable material and comprises a reagent, in particular a reagent selected from the group comprising an acid, a base, a salt, a sugar, a surfactant, a protein, a nucleic acid, an antimicrobial agent, in particular an antibacterial and/or an antifungal agent, a dye, a fluorophore, lanthanides, upconverting phosphor nanoparticles, colloidal gold, a cellulose nanobead, latex, a reagent for total protein quantification, an affinity molecule, in particular an antibody, an aptamer, an enzyme, a molecularly imprinted polymer, a ionophore, a pore or motor protein for nucleic acid sequencing, a nanoparticle, a microbead, more particularly said reagent is selected from an acid, a base, a salt, a sugar, a surfactant, a protein, a fluorophore, an upconverting phosphor nanoparticle, colloidal gold, a reagent for total protein quantification and an antibody, wherein in particular said reagent is in dried, lyophilized, gel or aqueous form, and wherein in particular said reagent is immobilised on a microbead or nanoparticle;
ii. a fastener zone (204) impermeable to water and/or delimited from reagent zone by a water impermeable barrier zone (208), said fastener zone (204) comprising, on said proximal surface (201), an adhesive (233) capable of fastening said sampling cover layer (200) removably to said rigid support (300);
g. applying an aqueous solution to said reagent zone (205), and applying said first vacuum to said distal surface (101) of said capture layer (100), wherein said aqueous solution is directed
i. from said reagent zone (205)
ii. via said analyte capture zone (105)
iii. to a liquid reservoir/absorber pad (402);
h. removing said analysis cover layer (200 P2) from said rigid support (300);
i. optionally repeating steps f to h 1 to 5 times, particularly 1 to 2 times using a different analysis cover layer (200 Pn);
j. detecting said analyte comprised in said analyte capture zone (105), particularly by a detection method selected from electrical detection, magnetic field detection, thermal detection and optical detection, more particularly by a detection method selected from impedance spectroscopy, voltammetry, Ion Selective Field Effect Transistors (ISFET)-based detection, magnetic field sensor, thermal contrast measurement, colour change, luminescence (including fluorescence and chemiluminescence) or turbidity measurement.

33. The method according to any one of items 29 to 32, wherein said analyte comprised in said analyte capture zone (105) has been obtained from a patient's skin or mucous membrane.

The invention claimed is:
1. A flexible planar patch comprising
a. a capture layer (100) having a proximal surface (101) and a distal surface (102),
wherein said capture layer (100) is characterized by a thickness of 10 μm to 2 mm,
and wherein said capture layer (100) comprises
i. an analyte capture zone (105) extending from said proximal surface (101) to said distal surface (102), said analyte capture zone (105) consisting of a first water permeable material, said first water permeable material comprising a ligand capable of binding specifically to an analyte; and
ii. a fastener zone (104) which is impermeable to water and/or delimited from said analyte capture zone by a water impermeable barrier zone (108), said fastener zone (104) comprising, on said proximal surface (101), an adhesive (133) capable of fastening said capture layer (100) removably to a surface, and
b. a cover layer (200) having a proximal surface (201) and a distal surface (202), said cover layer comprising, on said proximal surface (201), an adhesive (233) capable of fastening said cover layer (200) removably to said capture layer (100),
wherein said cover layer (200) comprises
a) a reagent zone (205) extending from said proximal surface (201) to said distal surface (202), said reagent zone (205) consisting of a second water permeable material, and
b) a fastener zone (204) which is impermeable to water and/or delimited from said reagent zone (205) by a water impermeable barrier zone (208).

2. The patch according to claim 1, wherein said analyte capture zone (105) is compartmentalized into a plurality of confined water permeable capture divisions (106), wherein each of said capture divisions (106) comprises said ligand capable of binding specifically to an analyte and is separated by a first divider (107) that is impermeable to water.

3. The patch according to claim 2, wherein said plurality of capture divisions (106) is divided into groups of capture divisions (111), wherein each of said groups of capture divisions (111) is separated by a second divider (109) that is impermeable to water, wherein said second divider (109) is formed by
a. a layer of hydrophobic material introduced in a reactive layer (110), wherein said layer of hydrophobic material extends from said proximal surface (101) to said distal surface (102) of said reactive layer (110),
b. an adherence layer (130), and/or
c. a reinforcement layer (120).

4. The patch according to claim 2, wherein at an interface of said proximal surface (101) of said capture layer (100) and said distal surface (202) of said cover layer (200), a capture division (106) of the plurality of capture division (106) and a reagent division (206) are in fluid connection, wherein the capture division (106) is sealed from the surrounding area by a water impermeable barrier comprising said first divider (107) and/or a second divider (109), and wherein the reagent division (206) is sealed from the surrounding area by a reagent divider (207).

5. The patch according to claim 2, wherein the analyte capture zone (105) comprises one of: 2-1000 capture divisions (106), and 2-256 capture divisions (106).

6. The patch according to claim 2, wherein said plurality of capture divisions (106) is divided into groups of capture divisions (111), wherein each of said groups of capture divisions (111) is separated by a second divider (109) that is impermeable to water.

7. The patch according to claim 6, wherein said plurality of capture divisions (106) is divided into one of: 2-50 groups of capture divisions (111), and 2-16 groups of capture divisions (111).

8. The patch according to claim 1, wherein said analyte capture zone (105) is located in the centre of said capture layer (100) and said fastener zone (104) is located at the perimeter of said capture layer (100).

9. The patch according to claim 1, wherein a peel adhesion between said cover layer (200) and said capture layer (100) is between 0.1 N/25 mm and 5 N/25 mm.

10. The patch according to claim 1, wherein said reagent zone (205) is compartmentalized into a plurality of confined water permeable reagent divisions (206), wherein each of said reagent divisions (206) is separated by a reagent divider (207) that is impermeable to water.

11. The patch according to claim 10, wherein each said reagent divisions (206) comprise a reagent.

12. The patch according to claim 11, wherein said reagent is in dried, lyophilized, gel or aqueous form.

13. The patch according to claim 11, wherein said reagent is immobilised on a microbead or nanoparticle.

14. The patch according to claim 11, wherein said reagent is selected from the group comprising an acid, a base, a salt, a sugar, a surfactant, a protein, a nucleic acid, an antimicrobial agent, a dye, a fluorophore, a lanthanide, an upconverting phosphor nanoparticle, colloidal gold, cellulose nanobeads, latex, a reagent for total protein quantification, an antibody, an aptamer, an enzyme, a molecularly imprinted polymer, an ionophore, a pore or motor protein for nucleic acid sequencing, a nanoparticle, and a microbead.

15. The patch according to claim 10, wherein each said reagent divider (207) is formed by
    a. a layer of hydrophobic material introduced in a reactive layer (210), wherein said layer of hydrophobic material extends from said proximal surface (201) to said distal surface (202) of said reactive layer (210),
    b. an adherence layer (230), and/or
    c. a reinforcement layer (220).

16. The patch according to claim 10, wherein said reagent zone (205) comprises one of: 2-144 reagent divisions (206), 2-64 reagent divisions (206), 2-36 reagent divisions, and 2-16 reagent divisions (206).

17. The patch according to claim 1, wherein said reagent zone (205) comprises an adaptor (501) designed to connect said reagent zone (205) to a confined volume and/or to an ultrasonic transducer.

18. The patch according to claim 1, wherein said capture layer (100) is attached to a rigid support (300) having a proximal surface (301) and a distal surface (302),
    wherein said rigid support (300) comprises
        a. a fastener zone (304) to which said proximal surface (101) of said capture layer (100) is attached, and
        b. a central opening (305) which is aligned with said analyte capture zone (105) of said capture layer (100).

19. The patch according to claim 1, wherein said capture layer (100) comprises
    I. an adherence layer (130) comprising said adhesive (133) and
    II. a reactive layer (110) comprising said analyte capture zone (105) and wherein said cover layer (200) comprises:
        a. an adherence layer (230) comprising said adhesive (233) and
        b. a reactive layer (210) comprising said reagent zone (205).

20. The patch according to claim 1, wherein the patch is configured as
    a. a patch for multiplex detection of analytes;
    b. a patch for detection of analytes on human or animal skin;
    c. a patch for detection of analytes by an immunological method and/or
    d. a diagnostic patch.

* * * * *